(12) United States Patent
Ishii

(10) Patent No.: US 11,481,957 B2
(45) Date of Patent: Oct. 25, 2022

(54) MEDICAL IMAGE PROCESSING APPARATUS AND STORAGE MEDIUM

(71) Applicant: CANON MEDICAL SYSTEMS CORPORATION, Otawara (JP)

(72) Inventor: Hideaki Ishii, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 274 days.

(21) Appl. No.: 16/833,732

(22) Filed: Mar. 30, 2020

(65) Prior Publication Data
US 2020/0312012 A1 Oct. 1, 2020

(30) Foreign Application Priority Data

Apr. 1, 2019 (JP) .............................. JP2019-070125
Mar. 23, 2020 (JP) .............................. JP2020-050665

(51) Int. Cl.
*G06T 15/08* (2011.01)
*G06T 7/564* (2017.01)
(Continued)

(52) U.S. Cl.
CPC ............ *G06T 15/08* (2013.01); *A61B 6/4014* (2013.01); *A61B 6/504* (2013.01); *A61B 6/541* (2013.01);
(Continued)

(58) Field of Classification Search
CPC ........ A61B 2090/364; A61B 2090/374; A61B 2090/3762; A61B 2090/378; A61B 2576/00; A61B 34/00; A61B 5/00; A61B 5/0044; A61B 5/02; A61B 5/02007; A61B 5/026; A61B 5/0261; A61B 5/0263; A61B 5/055; A61B 5/107; A61B 5/1075; A61B 5/1079; A61B 5/339; A61B 5/7246; A61B 5/7278; A61B 5/748; A61B 90/37; A61B 2576/023; A61B 6/03; A61B 6/4014;
(Continued)

(56) References Cited

U.S. PATENT DOCUMENTS 9,445,745 B2 * 9/2016 Cohen ...................... A61B 5/06
2014/0092228 A1 * 4/2014 Usuba ................. G06V 20/695
348/79

(Continued)

FOREIGN PATENT DOCUMENTS

JP 2014-113264 A 6/2014
JP 2015-531264 A 11/2015
(Continued)

*Primary Examiner* — Ming Wu
(74) *Attorney, Agent, or Firm* — Oblon, McClelland, Maier & Neustadt, L.L.P.

(57) ABSTRACT

A medical image processing apparatus of an embodiment includes processing circuitry. The processing circuitry is configured to acquire time-series medical images including blood vessels of an examination subject, the time-series medical images being fluoroscopically captured in at least one direction at a plurality of points in time, generate a blood vessel shape model including time-series variation information about the blood vessels in an analysis region of the blood vessels on the basis of the acquired time-series medical images, and perform fluid analysis of blood flowing through the blood vessels on the basis of the generated blood vessel shape model.

18 Claims, 14 Drawing Sheets

(51) Int. Cl.
*A61B 6/00* (2006.01)
*G06T 7/00* (2017.01)

(52) U.S. Cl.
CPC ............ *G06T 7/0016* (2013.01); *G06T 7/564* (2017.01); *G06T 2207/30104* (2013.01); *G06T 2210/41* (2013.01); *G06T 2211/404* (2013.01)

(58) Field of Classification Search
CPC ....... A61B 6/4441; A61B 6/467; A61B 6/481; A61B 6/487; A61B 6/504; A61B 6/5217; A61B 6/5288; A61B 6/541; G06T 15/08; G06T 2207/30104; G06T 2210/41; G06T 2211/404; G06T 7/0016; G16H 30/40; G16H 50/20
See application file for complete search history.

(56) References Cited

U.S. PATENT DOCUMENTS

| | | | | |
|---|---|---|---|---|
| 2015/0327780 | A1* | 11/2015 | Kano | A61B 90/37 600/407 |
| 2016/0166327 | A1* | 6/2016 | Keller | A61B 5/6876 623/1.1 |
| 2017/0112405 | A1* | 4/2017 | Sterrett | A61B 5/287 |

FOREIGN PATENT DOCUMENTS

| | | |
|---|---|---|
| JP | 2015-231524 A | 12/2015 |
| WO | WO 2014/042899 A2 | 3/2014 |

\* cited by examiner

MEDICAL IMAGE PROCESSING APPARATUS AND STORAGE MEDIUM

CROSS-REFERENCE TO RELATED APPLICATION

The present application claims priority based on Japanese Patent Application No. 2019-070125, filed on Apr. 1, 2019 and Japanese Patent Application No. 2020-050665, filed on Mar. 23, 2020, the content of which is incorporated herein by reference.

FIELD

Embodiments disclosed in the present description and drawings relate to a medical image processing apparatus, a medical image processing method, and a storage medium.

BACKGROUND

Technologies for analyzing the function and structure of a blood vessel using images have been known. In blood vessel analysis, a technology for fixing a function index of the blood vessel of an examination subject from time-series images including the blood vessels of the examination subject on the basis of information on correlations between physical indexes of blood vessels and function indexes of blood vessels with respect to blood circulation states has been known. In addition, a technology for temporarily constructing a dynamic model with respect to structural fluid analysis of an analysis target region on the basis of time-series form indexes, deformation indexes, and medical images and fixing latent variables with respect to a latent variable identification region such that a predicted value of a blood vessel form index and a predicted value of a blood flow index based on the constructed dynamic model match at least one of an observed value of the blood vessel form index and an observed value of the blood flow index, which are measured in advance, has been known. However, there are cases in which the above-described technology requires time and effort for measurement and an analysis method itself also requires time and effort and thus blood vessel analysis cannot be performed in an acute phase or the like.

DETAILED DESCRIPTION

A medical image processing apparatus of an embodiment includes processing circuitry. The processing circuitry is configured to acquire time-series medical images including blood vessels of an examination subject, the time-series medical images being fluoroscopically captured in at least one direction at a plurality of points in time, generate a blood vessel shape model including time-series variation information about the blood vessels in an analysis region of the blood vessels on the basis of the acquired time-series medical images, and perform fluid analysis of blood flowing through the blood vessels on the basis of the generated blood vessel shape model.

Hereinafter, a medical image processing apparatus and a storage medium of embodiments will be described with reference to the drawings.

First Embodiment

Figure 1:
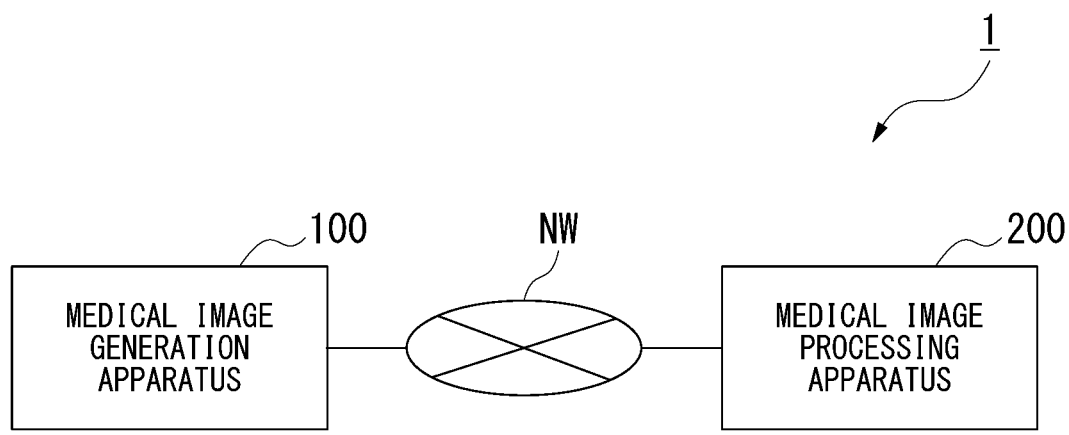
FIG. 1 is a diagram showing an example of a medical image processing system 1 including a medical image processing apparatus of a first embodiment.

FIG. 1 is a diagram showing an example of a medical image processing system 1 including a medical image processing apparatus of a first embodiment. The medical image processing system 1 includes a medical image generation apparatus 100 and a medical image processing apparatus 200. The medical image generation apparatus 100 and the medical image processing apparatus 200 are connected to each other through a network NW. The network NW includes, for example, a wide area network (WAN), a local area network (LAN), the Internet, a dedicated line, a wireless base station, a provider, and the like.

The medical image generation apparatus 100 is, for example, an X-ray diagnostic apparatus which generates medical images for diagnosing an examination subject using X-rays or the like. More specifically, the medical image generation apparatus 100 is, for example, an angiography apparatus which injects a contrast medium into the blood vessel of an examination subject and performs angiography. Although a case where the medical image generation apparatus 100 is an angiography apparatus is exemplified in the following description, the present invention is not limited thereto.

The medical image processing apparatus 200 is realized by one or a plurality of processors. For example, the medical image processing apparatus 200 may be a computer included in a cloud computing system or a computer (standalone computer) independently operating without depending on other apparatuses. Although the medical image processing system 1 includes one medical image generation apparatus 100 and one medical image processing apparatus 200 in the example of FIG. 1, the present invention is not limited thereto and the medical image processing system 1 may include a plurality of medical image generation apparatuses 100 and/or a plurality of medical image processing apparatuses 200. Further, the medical image generation apparatus 100 and the medical image processing apparatus 200 may be integrated into one body as a medical image diagnostic apparatus.

[Configuration of Medical Image Generation Apparatus]

Figure 2:
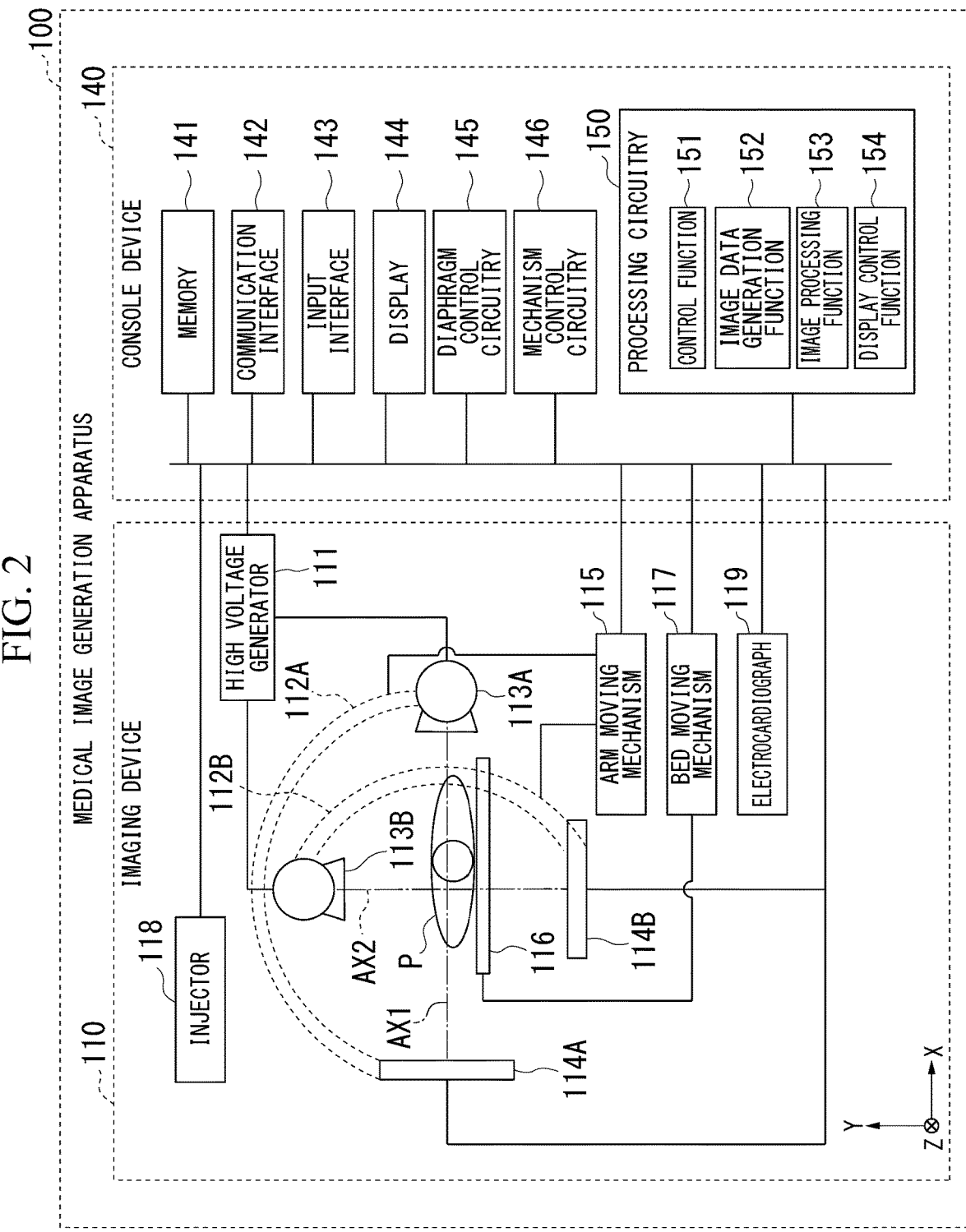
FIG. 2 is a diagram showing an example of a medical image generation apparatus 100 according to the first embodiment.

FIG. 2 is a diagram showing an example of the medical image generation apparatus 100 according to the first embodiment. The medical image generation apparatus 100 includes, for example, an imaging device 110 and a console device 140. Although the imaging device 110 includes a plurality of imaging systems (specifically, two imaging systems) in the example of FIG. 2, the present invention is not limited thereto and the imaging device 110 may include at least one imaging system. That is, the imaging device 110 in the first embodiment fluoroscopically captures medical images including the blood vessel of an examination subject which will be described later in at least one direction at a plurality of points in time.

The imaging device 110 includes, for example, a high voltage generator 111, a first arm 112A, a second arm 112B, a first X-ray generator 113A, a second X-ray generator 113B, a first X-ray detector 114A, a second X-ray detector 114B, an arm moving mechanism 115, a bed 116, a bed moving mechanism 117, an injector 118, and an electrocardiograph 119. There are cases below in which a combination of the first arm 112A, the first X-ray generator 113A, and the first X-ray detector 114A is referred to as a "first imaging system SA" and a combination of the second arm 112B, the second X-ray generator 113B, and the second X-ray detector 114B is referred to as a "second imaging system SB."

The high voltage generator 111 generates high voltages according to control of processing circuitry 150 and provides the generated high voltages to the first X-ray generator 113A and the second X-ray generator 113B. Voltage values provided to the first X-ray generator 113A and the second X-ray generator 113B may be the same or may be different.

The first arm 112A and the second arm 112B are holding devices having a curved shape or a bent shape such as a C shape in a part or all thereof, for example. The first arm 112A and the second arm 112B can individually rotate and move due to driving of the arm moving mechanism 115 according to control of mechanism control circuitry 146 which will be described later.

The first arm 112A holds the first X-ray generator 113A at one end thereof and holds the first X-ray detector 114A at the other end thereof such that it faces the first X-ray generator 113A. The first X-ray generator 113A includes, for example, a first X-ray tube (not shown) and a first collimator (not shown). The first X-ray tube receives application of a high voltage (tube voltage) and supply of tube current from the high voltage generator 111 and generates X-rays from an X-ray focus. The first collimator is attached to a radiation window of the first X-ray tube and adjusts an X-ray radiation field on the detection surface of the first X-ray detector 114A. It is possible to reduce unnecessary exposure to an examination subject P by adjusting the X-ray radiation field using the first collimator. The first X-ray detector 114A includes, for example, a plurality of X-ray detection elements. The plurality of X-ray detection elements are arranged in a two-dimensional array form. The detector in the two-dimensional array form is called a flat panel display (FPD). Each element of the FPD detects X-rays radiated from the first X-ray generator 113A and transmitted through an examination subject. Each element of the FPD outputs an electrical signal associated with a detected X-ray intensity. The first X-ray detector 114A may be configured from a combination of an image intensifier and a TV camera instead of the aforementioned FPD. A line connecting the focus of the first X-ray tube and the center of the detection surface of the first X-ray detector 114A is called a "first imaging axis AX1."

The second arm 112B holds the second X-ray generator 113B at one end thereof and holds the second X-ray detector 114B at the other end thereof such that it faces the second X-ray generator 113B. The second X-ray generator 113B includes, for example, a second X-ray tube (not shown) and a second collimator (not shown). Description of the second X-ray generator 113B is the same as the above description of the first X-ray generator 113A. Description of the second X-ray detector 114B is the same as the above description of the first X-ray detector 114A. A line connecting the focus of the second X-ray tube and the center of the detection surface of the second X-ray detector 114B is called a "second imaging axis AX2."

The arm moving mechanism 115 rotates and moves the first arm 112A and the second arm 112B to predetermined positions on three-dimensional coordinates (XYZ coordinates) according to control of the mechanism control circuitry 146 which will be described later. The arm moving mechanism 115 rotates and moves the arms such that an imaging range corresponding to the X-ray radiation field of the first imaging system SA and an imaging range corresponding to the X-ray radiation field of the second imaging system SB include the same range. In addition, the arm moving mechanism 115 rotates and moves each arm such that the first imaging axis AX1 intersects the second imaging axis AX2 and an angle formed by the intersection of the two axes becomes equal to or greater than a predetermined angle.

The bed 116 movably supports a top board on which the examination subject P is mounted. The top board is moved by driving the bed moving mechanism 117 according to control of the mechanism control circuitry 146. The examination subject P is mounted facing upward on the top board in the example of FIG. 2.

The injector 118 is a device for injecting a contrast medium from a catheter inserted into the examination subject P, for example. The contrast medium injection from the injector 118 is executed according to an injection instruction from the processing circuitry 150. Specifically, the injector 118 executes contrast medium injection according to a contract medium injection start instruction and an injection stop instruction acquired from the processing circuitry 150, and an additional contrast medium injection condition including an injection speed and the like. The injector 118 may start and stop injection according to injection instructions directly input by a user (operator) to the injector 118.

The electrocardiograph 119 acquires an electrocardiogram (ECG) of the examination subject P to which a terminal which is not shown is attached and outputs electrocardiogram data in which the acquired ECG is associated with time information to the processing circuitry 150.

The console device 140 includes, for example, a memory 141, a communication interface 142, an input interface 143, a display 144, diaphragm control circuitry 145, the mechanism control circuitry 146, and the processing circuitry 150. The memory 141 is realized by, for example, a semiconductor memory element such as a random access memory (RAM) or a flash memory, a hard disk, an optical disc, or the like. The memory 141 stores, for example, images (an example of medical images) captured by the first imaging system SA and the second imaging system SB, programs, various types of other information, and the like. Such data may be stored in an external memory with which the medical image generation apparatus 100 can communicate instead of the memory 141 (or in addition to the memory 141). The external memory is controlled by a cloud server which manages the external memory by receiving a read/write request, for example.

The communication interface 142 includes, for example, a communication interface such as a network interface controller (NIC). The communication interface 142 communicates with the imaging device 110 and the medical image processing apparatus 200 and outputs acquired information to the processing circuitry 150. The communication interface 142 may transmit information to other devices connected through the network NW under the control of the processing circuitry 150.

The input interface 143 receives various input operations from a user and outputs electrical signals representing details of the received input operations to the processing circuitry 150. For example, the input interface 143 receives input operations such as a collection condition when imaging data is collected and an image processing condition in which predetermined processing is performed on images. For example, the input interface 143 may be realized by a mouse, a keyboard, a touch panel, a trackball, a switch, a button, a joystick, a foot pedal, a camera, an infrared sensor, a microphone, or the like. The input interface 143 may be provided in the imaging device 110. In addition, the input interface 143 may be realized by a display device (for example, a tablet terminal) which can wirelessly communicate with the main body of the console device 140.

The display 144 displays various types of information. For example, the display 144 displays a medical image (for example, an angiographic image) generated by the processing circuitry 150, a graphical user interface (GUI) image through which various operations are received from a user, and the like. For example, the display 144 may be a liquid crystal display, a cathode ray tube (CRT), an organic electroluminescence (EL) display, or the like. The display 144 may be provided in the imaging device 110. The display 144 may be of a desktop type or a display device (for example, a tablet terminal) which can wirelessly communicate with the main body of the console device 140.

The diaphragm control circuitry 145 controls a radiation range of X-rays radiated to the examination subject P (X-ray radiation field) on the basis of control of the processing circuitry 150, for example. Information about the radiation range is also called a field of view (FOV) information. The diaphragm control circuitry 145 controls the radiation range of X-rays by performing, for example, control such as adjustment of apertures of diaphragm blades included in the first collimator of the first X-ray generator 113A and the second collimator of the second X-ray generator 113B.

The mechanism control circuitry 146 controls the arm moving mechanism 115 and the bed moving mechanism 117 on the basis of control of the processing circuitry 150 such that they change imaging ranges in the first imaging system SA and the second imaging system SR, relative positions, imaging angles, and the like of the first imaging system SA and the second imaging system SB with respect to the examination subject P.

The processing circuitry 150 controls the overall operation of the medical mage generation apparatus 100. The processing circuitry 150 includes, for example, a control function 151, an image data generation function 152, an image processing function 153, and a display control function 154. The processing circuitry 150 realizes these functions by a hardware processor executing a program stored in the memory 141, for example. The hardware processor refers to circuitry such as a central processing unit (CPU), a graphics processing unit (GPU), an application specific integrated circuit (ASIC), or a programmable logic device (for example, a simple programmable logic device (SPLD) or a complex programmable logic device (CPLD), or a field programmable gate array (FPGA)), for example. The program may be directly incorporated into the circuit of the hardware processor instead of being stored in the memory 141. In this case, the hardware processor realizes the functions by reading and executing the program incorporated into the circuit thereof. The hardware processor is not limited to a configuration of a single circuit and may be configured as a single hardware processor according to a combination of a plurality of independent circuits to realize the respective functions. Further, a plurality of components may be integrated into a single hardware processor to realize the respective functions.

Components included in the console device 140 or the processing circuitry 150 may be realized by a plurality of distributed hardware circuits. The processing circuitry 150 may be realized by a processing device which can communicate with the console device 140 instead of a component included in the console device 140. The processing device may be, for example, a work station connected to a single medical image generation apparatus or a device (for example, a cloud server) which is connected to a plurality of medical image generation apparatuses and collectively executes processes equivalent to those of the processing circuitry 150 which will be described below.

The control function 151 controls various functions of the processing circuitry 150 on the basis of input operations received through the input interface 143. Specifically, the control function 151 causes a plurality of imaging systems (for example, the first imaging system SA and the second imaging system SB) to capture medical images including the blood vessel of the examination subject in a plurality of directions (for example, the first imaging axis AX1 and the second imaging axis AX2) at a plurality of points in time, for example. In this case, the control function 151 performs predetermined control for the high voltage generator 111, the injector 118, the electrocardiograph 119, the diaphragm control circuitry 145, and the mechanism control circuitry 146 on the basis of details of instructions, details of imaging, and the like from the input interface 143 and the like. In addition, the control function 151 causes the image data generation function 152, the image processing function 153, and the display control function 154 to execute predetermined processes on captured time-series images. Further, the control function 151 performs control of transmitting captured images, parameter information (for example, details of diaphragm control and details of mechanism control) during imaging, measurement results of the electrocardiograph 119, and the like to the medical image processing apparatus through the network NW, and the like.

The image data generation function 152 generates image data using electrical signals converted from X-rays according to the first X-ray detector 114A and the second X-ray detector 114B and stores the generated image data in the memory 141. For example, the image data generation function 152 performs current/voltage conversion, analog/digital (A/D) conversion, and parallel/serial conversion on electrical signals received from the first X-ray detector 114A and the second X-ray detector 114B to generate image data. For example, the image data generation function 152 generates image data (mask image) captured in a state in which a contrast medium is not injected and image data (contrast image) captured in a state in which the contrast medium has been injected. Then, the image data generation function 152 stores the generated mask image and contrast image in the memory 141.

The image processing function 153 performs various types of image processing on image data stored in the memory 141. For example, the image processing function 153 generates a difference image by reading the mask image and the contrast image stored in the memory 141 and executing subtraction (log subtraction) thereon. The image processing function 153 can minimize an error in registration due to a body motion using one frame immediately before contrast medium injection as a mask image. In addition, the image processing function 153 may execute noise reduction processing using image processing filters such as a moving average (smoothing) filter, a Gaussian filter, and a median filter. The image processing function 153 may execute preprocessing including dislocation correction and noise removal on a plurality of X-ray image groups captured over time using a contrast medium.

The display control function 154 controls display details displayed on the display 144 and a display mode. Specifically, the display control function 154 causes the display 144 to display a GUI image through which an instruction from a user is received and image data generated by the image data generation function 152, for example. In addition, the display control function 154 may cause the display 144 to display an analysis result received from the medical image processing apparatus 200.

[Configuration of Medical Image Processing Apparatus]

Figure 3:
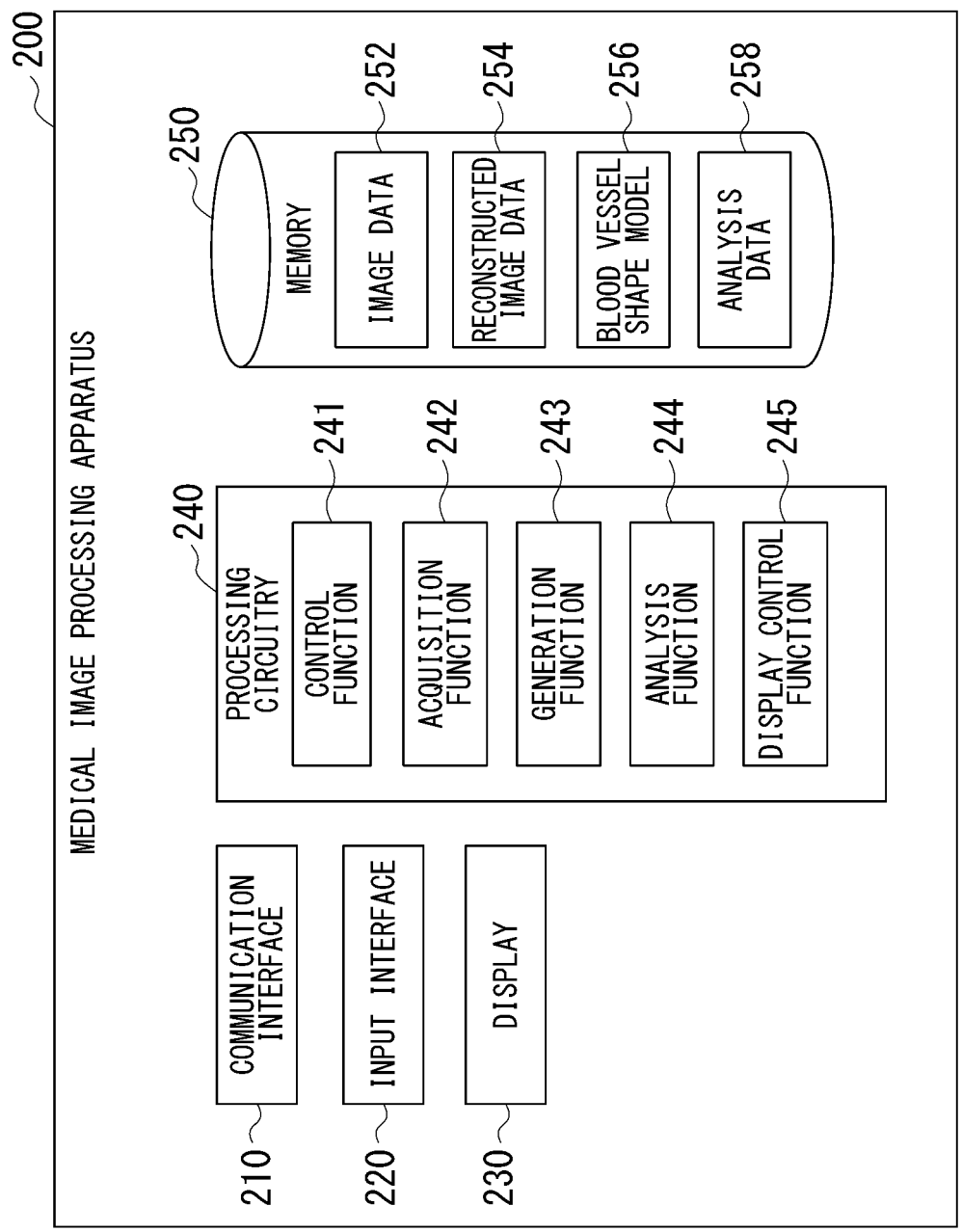
FIG. 3 is a diagram showing an example of a medical image processing apparatus 200 according to the first embodiment.

FIG. 3 is a diagram showing an example of the medical image processing apparatus 200 according to the first embodiment. The medical image processing apparatus 200 includes, for example, a communication interface 210, an input interface 220, a display 230, processing circuitry 240, and a memory 250.

The communication interface 210 includes, for example, a communication interface such as an NIC. The communication interface 210 communicates with the medical image generation apparatus 100 through the network NW and receives information from the medical image generation apparatus 100. The communication interface 210 outputs the received information to the processing circuitry 240. In addition, the communication interface 210 may transmit information to other devices connected through the network NW under the control of the processing circuitry 240. The other devices may be, for example, terminal devices which can be used by image readers such as doctors and nurses.

The input interface 220 receives various input operations from a user, converts the received input operations into electrical signals and outputs the electrical signals to the processing circuitry 240. For example, the input interface 220 may be realized by a mouse, a keyboard, a trackball, a switch, a button, a joystick, a touch panel, or the like. The input interface 220 may be realized by a user interface that receives audio input, such as a microphone, for example. In a case in where the input interface 220 is a touch panel, the display 230 may be integrated with the input interface 220.

The display 230 displays various types of information. For example, the display 230 displays an image and a blood vessel shape model generated by the processing circuitry 240, analysis results, and the like, a GUI for receiving various input operations from a user, and the like. For example, the display 230 may be an LCD, a CRT display, an organic EL display, or the like.

The processing circuitry 240 includes, for example, a control function 241, an acquisition function 242, a generation function 243, an analysis function 244, and a display control function 245. The acquisition function 242 is an example of an "acquirer." The generation function 243 is an example of a "generator." The analysis function 244 is an example of an "analyzer." The display control function 245 is an example of a "display controller". These functions (components) are realized by a hardware processor (or a processor circuit) such as a CPU or a GPU executing a program (software) stored in the memory 250. Some or all of these functions may be realized by hardware (circuitry) such as an LSI circuit, an ASIC and an FPGA or software and hardware in cooperation. The aforementioned program may be stored in the memory 250 in advance or stored in a detachable storage medium such as a DVD or a CD-ROM and installed in the memory 250 from the storage medium by mounting the storage medium in a drive device of the medical image processing apparatus 200.

The memory 250 is realized by a semiconductor memory element such as a RAM or a flash memory, a hard disk, an optical disc, or the like. These non-transitory storage media may be realized by other storage devices connected through the network NW, such as an NAS and an external storage server device. Further, the memory 250 may include transitory storage media such as a ROM or a register. For example, image data 252, reconstructed image data 254, a blood vessel shape model 256, analysis data 258, a program, various other types of information, and the like are stored in the memory 250.

The control function 241 controls various functions of the medical image processing apparatus 200 on the basis of input operations received through the input interface 220. For example, the control function 241 controls acquisition of image data through the communication interface 210, storage of the acquired image data in the memory 250, and the like. In addition, the control function 241 generates an image of a three-dimensional shape of blood vessels (for example, reconstructed image data), a blood vessel shape model, and the like by reading the image data 252 stored in the memory 250 and performing various types of image processing on the read image data 252, for example. In addition, the control function 241 causes image analysis using the generated blood vessel shape model to be performed, causes an image for displaying an analysis result to be generated, and causes the generated image to be output to the display 230 and the medical image generation apparatus 100.

The acquisition function 242 causes the communication interface 210 to communicate with the medical image generation apparatus 100 and acquires images including the blood vessel of the examination subject and electrocardiogram data captured by the first imaging system SA and the second imaging system SB at a plurality of points in time and information on diaphragm control, mechanism control, and the like during image capturing from the medical image generation apparatus 100 that is a communication counterparty. The acquired information is stored in the memory 250 as the image data 252 associated with time information.

The generation function 243 reconstructs a three-dimensional image using images captured by the first imaging system SA and the second imaging system SB. In addition, the generation function 243 generates the blood vessel shape model 256 in which blood vessels included in the reconstructed three-dimensional image are coupled and causes the memory 250 to store the generated blood vessel shape model 256. In addition, the generation function 243 generates the blood vessel shape model 256 including time-series variation information about blood vessels in an analysis range of blood vessels (for example, for each branch). The generation function 243 updates the blood vessel shape model 256 on the basis of a predetermined update condition. Functions of the generation function 243 will be described in detail later.

The analysis function 244 analyzes a blood vessel shape of the examination subject P using the blood vessel shape model 256 and causes the memory 250 to store an analysis result as the analysis data 258. Functions of the analysis function 244 will be described in detail later.

The display control function 245 causes the display 230 to display the image data 252 received from the medical image generation apparatus 100, the reconstructed image data 254, the blood vessel shape model 256, the analysis data 258, and the like and causes them to be transmitted to the medical image generation apparatus 100. Functions of the display control function 245 will be described in detail later.

Figure 4:
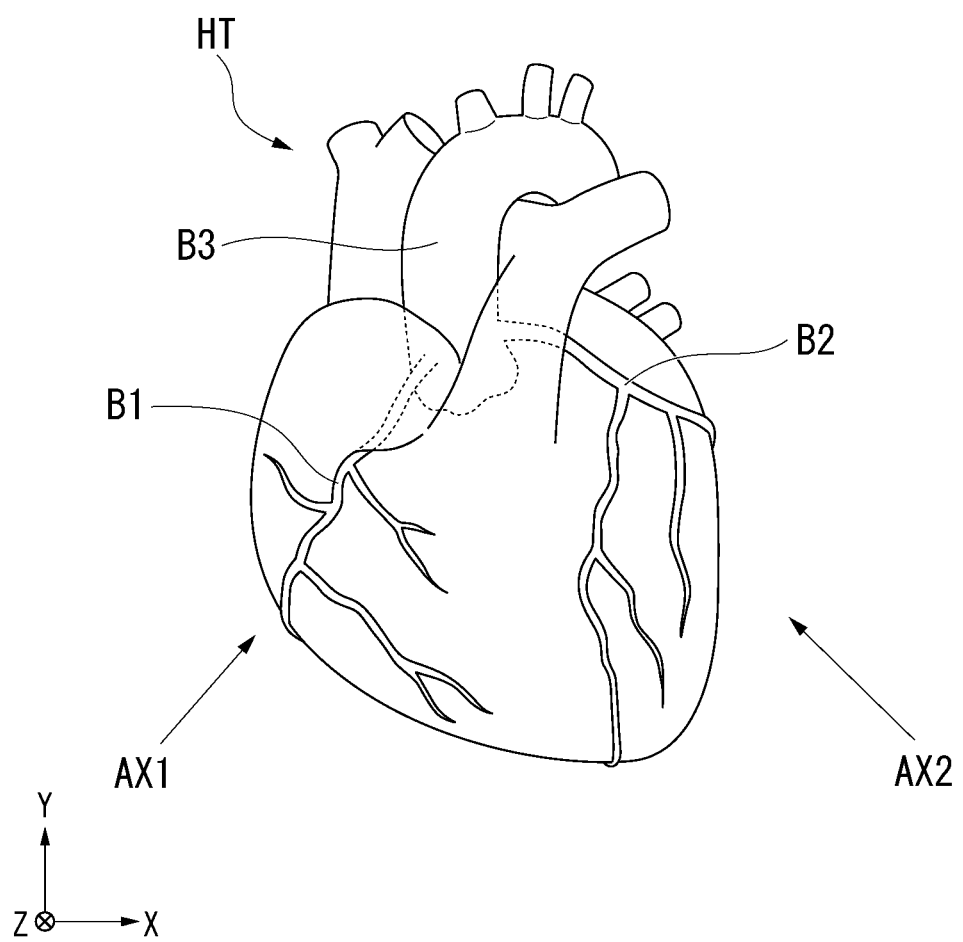
FIG. 4 is a diagram for describing capturing of images using a first imaging system SA and a second imaging system SB.

Hereinafter, processing in the medical image processing apparatus 200 will be described in detail. The medical image processing apparatus 200 acquires angiographic images (hereinafter referred to as blood vessel images) including the blood vessel of the examination subject P at a plurality of points in time, which are generated by the medical image generation apparatus 100 and captured by the first imaging system SA and the second imaging system SB in different directions. FIG. 4 is a diagram for describing capturing of images using the first imaging system SA and the second imaging system SB. As an example, FIG. 4 schematically shows blood vessels B1 to B3 with respect to a heart HT of the examination subject P. The blood vessel B1 represents the right coronary artery, the blood vessel B2 represents the left coronary artery, and the blood vessel B3 represents the ascendens aorta. Although blood vessel analysis in the right coronary artery and the left coronary artery will be described below, the present invention is not limited thereto and can be applied to other blood vessels (for example, the aorta, the cerebral blood vessel, and the liver artery).

For example, a user performs treatment, examination, a medical procedure, or the like on the coronary arteries, peripheral vascular system, and the like of the examination subject, for example, while viewing blood vessel images captured by the imaging device 110 of the medical image generation apparatus 100. Blood vessel images include an X-ray image collected under contrast radiography and an X-ray image collected without contrast radiography. An X-ray image collected under contrast radiography means a contrast X-ray image and an X-ray image collected by the medical image generation apparatus 100 without contrast radiography means a noncontrast X-ray image.

The medical image generation apparatus 100 generates a group of time-series blood vessel images (so-called a moving image) by imaging the heart HT of the examination subject P using the first imaging system SA and the second imaging system SB in different directions (the first imaging axis AX1 and the second imaging axis AX2) and transmits the generated moving image and measurement information such as electrocardiogram data measured by the electrocardiograph 119, details of diaphragm control during imaging, and details of mechanism control to the medical image processing apparatus 200. In the medical image generation apparatus 100, rotation and movement of the first arm 112A and the second arm 112B are performed such that an angle formed by the intersection of the first imaging axis AX1 and the second imaging axis AX2 becomes equal to or greater than a predetermined angle. The predetermined angle is, for example, an angle set to about 45 degrees. Accordingly, it is possible to more accurately generate a three-dimensional shape of blood vessels included in blood vessel images using the first imaging system SA and the second imaging system SB. The acquisition function 242 of the medical image processing apparatus 200 acquires measurement data such as a blood vessel image group and electrocardiogram data from the medical image generation apparatus 100 and causes the memory 250 to store the acquired data as the image data 252.

Figure 5:
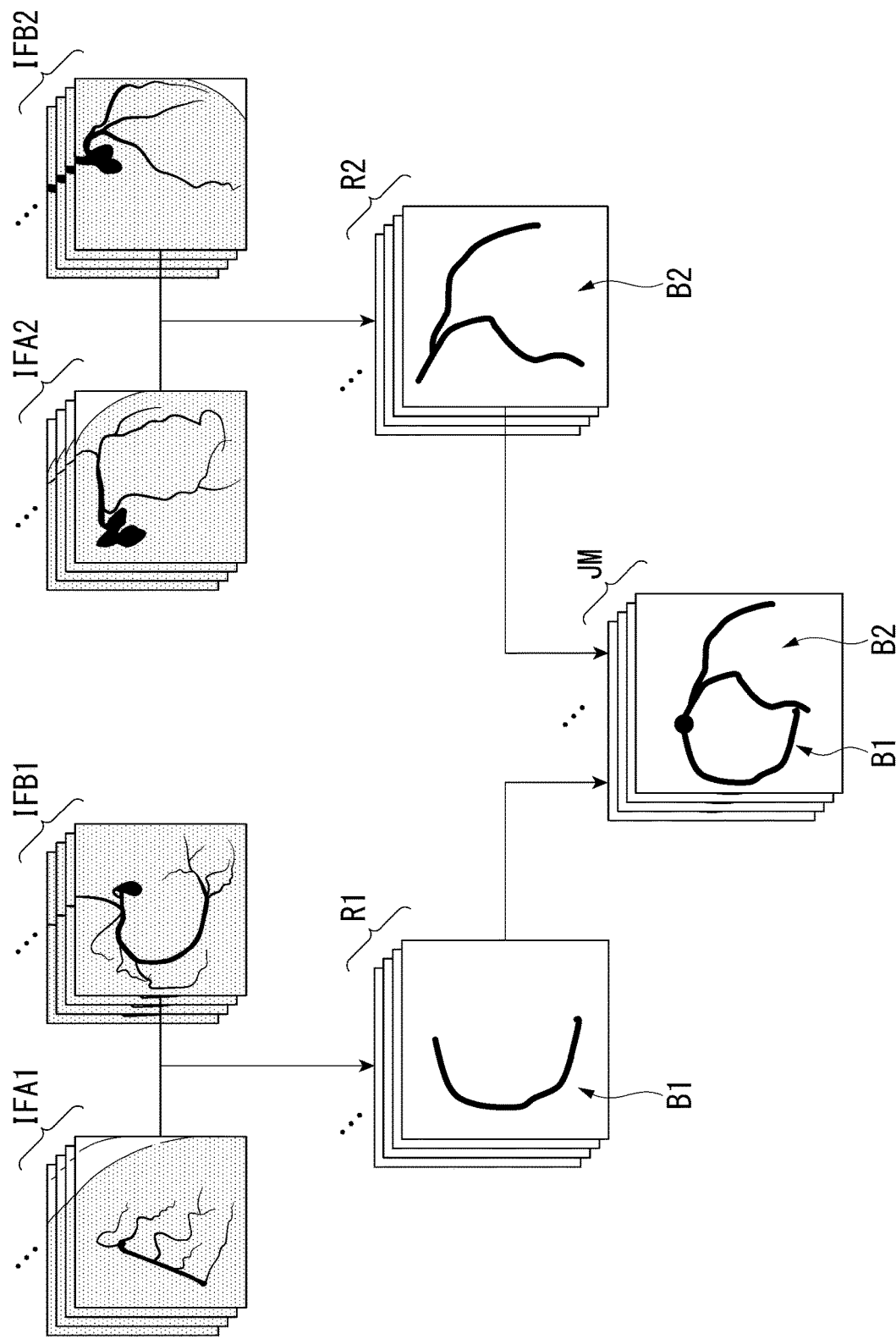
FIG. 5 is a diagram for describing a generation function 243.

Next, the generation function 243 will be described in detail. The generation function 243 reconstructs a three-dimensional blood vessel image on the basis of a blood vessel image group IFA including blood vessels of the examination subject P at a plurality of points in time captured by the first imaging system SA and a blood vessel image group IFB including the blood vessels of the examination subject P at a plurality of points in time captured by the second imaging system SB. FIG. 5 is a diagram for describing the generation function 243. In the example of FIG. 5, a blood vessel image group IFA1 is an image when the blood vessel B1 (right coronary artery) has been subjected to angiography at the right anterior oblique position (on the side of the first imaging axis AX1) and a blood vessel image group IFB1 is an image when the blood vessel B1 has been subjected to angiography at the left anterior oblique position (on the side of the second imaging axis AX2). A blood vessel image group IFA2 is an image when the blood vessel B2 (left coronary artery) has been subjected to angiography at the right anterior oblique position and a blood vessel image group IFB2 is an image when the blood vessel B2 has been subjected to angiography at the left anterior oblique position. Although the right coronary artery and the left coronary artery are shown in the example of FIG. 5, images captured in two directions may be acquired with respect to other blood vessels.

Next, the generation function 243 reconstructs blood vessel images included in an imaging range on the basis of the blood vessel image group IFA1 and the blood vessel image group IFB1 of the right coronary artery captured in two directions and generates blood vessel images R1 in a three-dimensional shape (hereinafter referred to as reconstructed image data). Further, the generation function 243 synchronizes heartbeat phases of the two blood vessel image groups with each other on the basis of ECG information included in electrocardiogram data measured by the electrocardiograph 119 to reconstruct three-dimensional images.

Here, since the blood vessel image group IFA1 and the blood vessel image group IFB1 are captured by different imaging systems (the first imaging system SA and the second imaging system SB), the images may have different sizes. Accordingly, the generation function 243 corrects the sizes (imaging range and FOV information) of one or both of the image groups such that the blood vessel image group IFA1 and the blood vessel image group IFB1 have the same size or similar sizes using surrounding blood vessels (for example, aorta) other than target blood vessels included in the images, surrounding human body structures (for example, part shapes of a bone such as the costa, the heart, and the like), and the like. Accordingly, it is possible to reduce an error in blood vessel sizes due to a difference between imaging systems.

Figure 6:
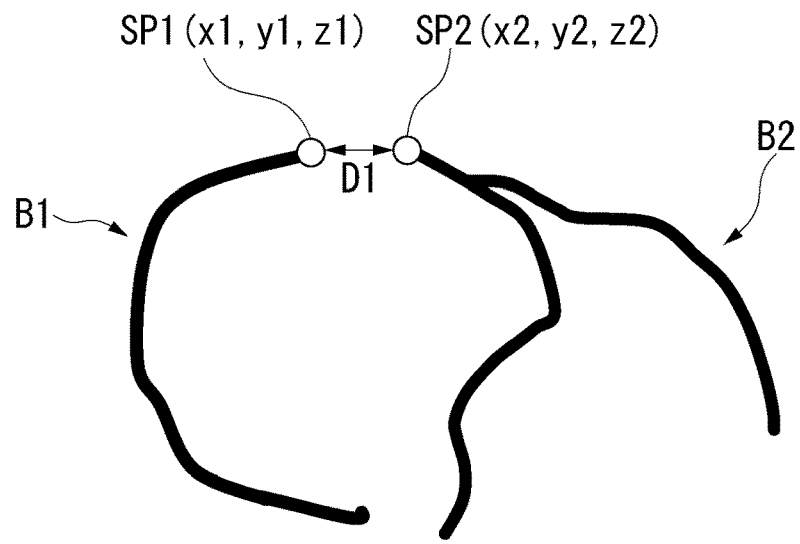
FIG. 6 is a diagram for describing coupling of two blood vessels.

The generation function 243 performs processing the same as the above-described processing of generating the reconstructed image data R1 using the blood vessel image group IFA2 and the blood vessel image group IFB2 to generate reconstructed image data R2. The generation function 243 reads image data of a plurality of time phases collected over time and performs image processing on the read image data of the plurality of time phases to extract time-series reconstructed image data. Next, the generation function 243 generates the three-dimensional blood vessel shape model 256 by coupling areas of blood vessels (blood vessels areas) in the analysis area on the basis of a positional relationship between the ends of blood vessels included in the two pieces of reconstructed image data R1 and R2. FIG. 6 is a diagram for describing coupling of two blood vessels. The generation function 243 estimates three-dimensional positions of the fore-ends (entrances of flow paths in the image) SP1 and SP2 of the blood vessels B1 and B2 on the basis of, for example, changes in the position of a contrast medium injected into the blood vessels with an elapse of time (flow of the contrast medium). Then, the generation function 243 calculates a distance D1 between estimated three-dimensional coordinates (x1, y1, z1) of the fore-end SP1 and estimated three-dimensional coordinates (x2, y2, z2) of the fore-end SP2 and determines that the fore-end SP1 and the fore-end SP2 are coupled to each other in a case where the distance D1 is equal to or less than a first predetermined distance Dth1.

Figure 7:
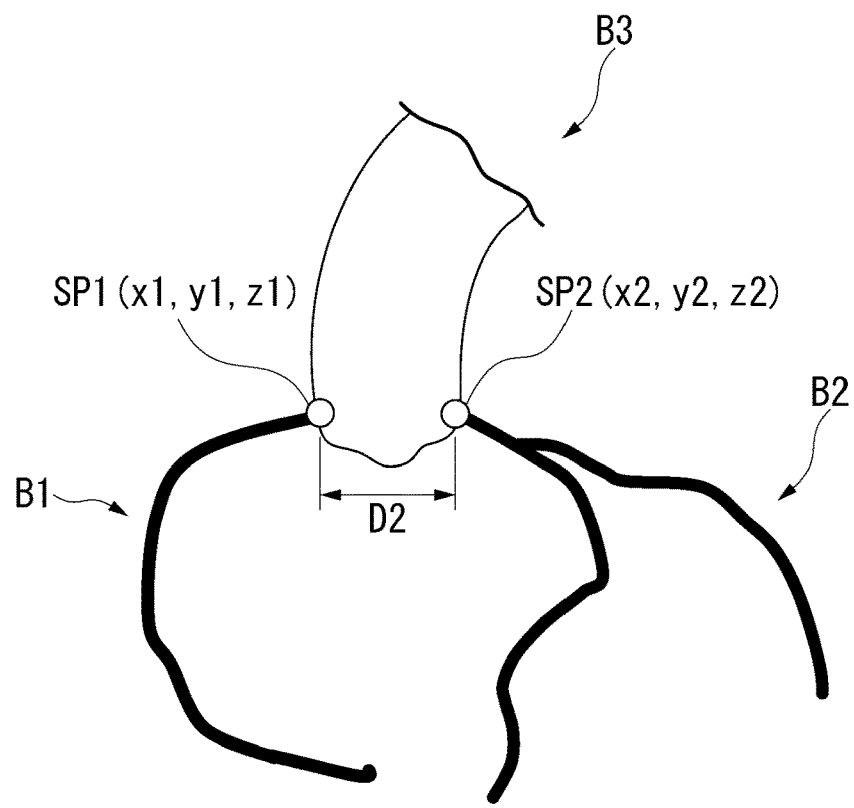
FIG. 7 is a diagram showing an example of a case where two blood vessels can be regarded to be coupled to each other.

The generation function 243 may regard the two blood vessels to be coupled to each other if it is estimated that they are coupled to each other through another blood vessel even when the distance between the fore-end SP1 and the fore-end SP2 is greater than the first predetermined distance Dth1. FIG. 7 is a diagram showing an example of a case where two blood vessels can be regarded to be coupled to each other. For example, the generation function 243 regards the fore-end SP1 and the fore-end SP2 to be coupled to each other in a case where it is analyzed that the fore-end SP1 and the fore-end SP2 are coupled through another blood vessel (ascendens aorta) B3 according to image analysis (for example, feature analysis through color difference, and edge extraction, and the like) although the distance between the three-dimensional position (x1, y1, z1) of the fore-end SP1 of the blood vessel B1 and the three-dimensional position (x2, y2, z2) of the fore-end SP2 of the blood vessel B2 is a distance D2 greater than the first predetermined distance Dth1.

In addition, the generation function 243 may regard the fore-end SP1 and the fore-end SP2 to be coupled to each other when presence of a medical member such as a stent ST1 is recognized from image analysis instead of (or in addition to) coupling through the aforementioned other blood vessel B3.

The generation function 243 may not reproduce a blood vessel positional relationship itself of a living body with respect to a blood vessel positional relationship after coupling of the blood vessels B1 and B2. This is because it is important to realize more appropriate fluid analysis using a three-dimensional model in which blood vessels are determined to be coupled in blood vessel analysis processing in the first embodiment, and importance of reconstruction of a three-dimensional blood vessel image in which fore-ends are pseudo-coupled is low. Accordingly, the generation function 243 may just connect fore-ends of blood vessels as flow paths when the fore-ends are connected, couples the fore-ends at the same coordinates of a three-dimensional model, for example, in a case where the distance D1 between the fore-ends is equal to or less than the predetermined distance Dth1, and couples the fore-ends through another flow path (for example, a dummy flow path) when the distance D1 is greater than the predetermined distance Dth1. In a case where the distance is the distance D2 and another blood vessel or a medical member is not present between the fore-ends, the generation function 243 does not couple the fore-ends. The generation function 243 performs the above-described blood vessel couple for each blood vessel in the reconstructed image data 254.

Figure 8:
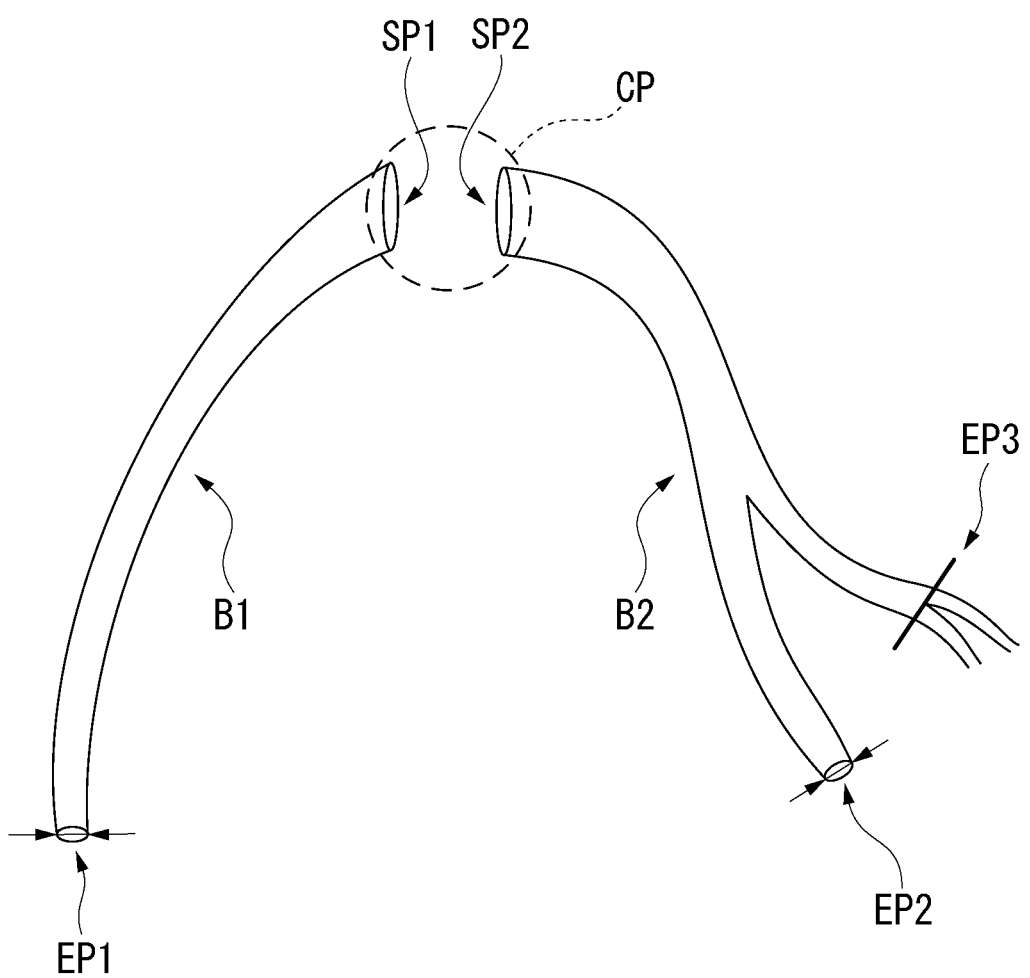
FIG. 8 is a diagram for describing acquisition of the position of a distal end.

Next, the generation function 243 acquires a three-dimensional position of a distal end of a blood vessel in the analysis area. FIG. 8 is a diagram for describing acquisition of the position of a distal end. The example of FIG. 8 schematically shows parts of the blood vessels B1 and B2. The generation function 243 acquires the length of a diameter around one pixel (e.g., short diameter) of an image included in the blood vessel shape model 256 on the basis of, for example, FOV information of the image data 252, and the like. Then, the generation function 243 recognizes positions at which the diameters of the blood vessels B1 and B2 are equal to or less than a predetermined diameter when the blood vessels B1 and B2 are searched from fore-ends (entrances) SP1 and SP2 or positions at which they are greater than a predetermined diameter when they are searched from the distal ends as distal ends EP of the blood vessels. In a case where a blood vessel has a branching part and the diameter of the blood vessel after branching is recognized as equal to or less than a predetermined diameter, the generation function 243 may estimate the position of the branching point as a distal end. In the example of FIG. 8, the generation function 243 recognizes a distal end EP1 of the blood vessel B1 and distal ends EP2 and EP3 of the blood vessel B2 according to the above-described analysis processing. Since it is possible to exclude thin blood vessels from analysis targets by setting distal ends, it is possible to improve the accuracy of information about blood vessels analyzed from image data.

Next, the generation function 243 acquires related information (hereinafter, blood vessel related information) at the positions of the blood vessels B1 and B2 on the basis of the reconstructed image data 254. The blood vessel related information includes, for example, time-series variation information about blood vessels. The blood vessel related information according to the first embodiment includes, for example, shape information of paths between fore-ends to distal ends. Shape information includes, for example, information such as blood vessel cross-sectional areas of the entrance and exit of a blood vessel, variation coefficients of cross-sectional areas over time, the twist, curvature and length of a blood vessel, and the like. The blood vessel related information may include information on a boundary condition at entrances (fore-ends) and exits (distal ends) of flow paths analyzed by the analysis function 244 which will be described later, and predetermined other positions, and the like. The boundary condition includes flow velocities and flow rates of blood flow in blood vessels, for example.

Figure 9:
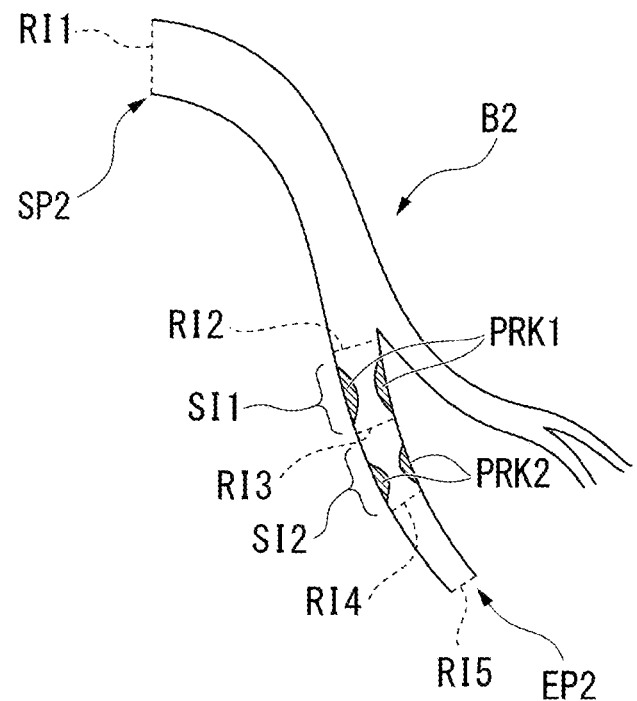
FIG. 9 is a diagram for describing acquisition of blood vessel related information.

FIG. 9 is a diagram for describing acquisition of blood vessel related information. Although FIG. 9 shows an example in which blood vessel related information at predetermined positions RI1 to RI5 between the fore-end SP2 to the distal end EP2 of the blood vessel B2 is acquired, positions and the number of pieces of blood vessel related information for analysis are not limited thereto. It is assumed that blood vessel related information is acquired in the same manner with respect to other target blood vessels. The generation function 243 extracts cross-sectional area variation coefficients at the predetermined positions RI1 to RI5 of the blood vessel B2 from the time-series reconstructed image data 254. The type of the blood vessel related information may be incorporated in the system in advance or interactively defined by a user. The aforementioned predetermined positions RI may be positions automatically derived on the basis of the shape and distance of the blood vessel or designated according to an instruction of the user through the input interface 220.

The generation function 243 generates the blood vessel shape model 256 in which the aforementioned blood vessel related information is associated with a three-dimensional blood vessel shape obtained by coupling blood vessels and causes the memory 250 to store the generated blood vessel shape model 256. The blood vessel shape model 256 is a three-dimensional blood vessel shape model including variations in the cross-sectional areas of blood vessels. Injection of a contrast medium through the injector 118 is intermittently performed during imaging performed by the first imaging system SA and the second imaging system SB. Accordingly, the processing circuitry 240 performs processing from acquisition of image data to generation of the blood vessel shape model 256 in association with a contrast medium injection timing. By generating the latest blood vessel shape model 256 in this manner, it is possible to obtain analysis results with higher accuracy using the analysis function 244 which will be described later.

Next, the analysis function 244 will be described in detail. The analysis function 244 performs fluid analysis of blood flowing through a blood vessel using the blood vessel shape model 256. For example, the analysis function 244 acquires a flow rate and a flow velocity of the blood flowing through the blood vessel through fluid analysis from variations in the cross-sectional areas at the predetermined positions RI1 to RI5 using characteristics that a flow rate and a flow velocity at a position can be estimated from variations in cross-sectional areas generated by the generation function 243. The analysis function 244 may acquire the flow rate and the flow velocity using a predetermined function having variations in cross-sectional areas as inputs and having a flow rate and a flow velocity as outputs. The analysis function 244 may acquire only one of the flow rate and the flow velocity using the variations in the cross-sectional areas.

The analysis function 244 derives a fractional flow reserve (FFR) on the basis of the blood vessel shape model 256. The FFR is an index by which a degree to which blood flow is hindered due to a lesion (for example, constriction, plaque, or the like) is assumed, is defined as a ratio of a flow rate when there is a lesion to a flow rate when there is no lesion, and is derived according to "FFR32 Qs/Qn ... (1)." In Equation (1), "Qn" represents a flow rate when there is no lesion and "Qs" represents a flow rate when there is a lesion. For example, the analysis function 244 derives the FFR using flow rates at the predetermined positions RI1 to RI5 of the blood vessel B2 included in the blood vessel shape model 256. The flow rate (right-answer data of flow rates) when there is no lesion may be set in advance using blood vessel related information such as cross-sectional areas and shapes or estimated from flow rates of other blood vessels or flow rates at other positions of the same blood vessel.

The FFR value derived in the first embodiment is not limited to a value using the above-described calculation method, and the calculation method is not limited thereto, for example, if the FFR value is a pressure index value indicating a comparison between a pressure at a point on the upstream side of a blood vessel and a pressure at a point on the downstream side. For example, the analysis function 244 may calculate a pressure ratio with respect to the examination subject in a rest state or assume a pressure value of the upstream side or the downstream side from another value or replace it with another value to calculate it.

The analysis function 244 may calculate AFFR that is a difference between FFRs at neighboring positions for each of the predetermined positions RI1 to RI5. Accordingly, the analysis function 244 can extract sections SI1 and SI2 in which constriction is present (hereinafter referred to as constriction sections), plaques PRK1 and PRK2, and the like in each section from the ΔFFR. In addition, ΔFFR calculated by the analysis function 244 can be used, for example, for evaluation of the constriction sections SI1 and SI2. For example, in a case where a plurality of constriction sections SI1 and SI2 are present in the blood vessel B2, as shown in FIG. 9, the analysis function 244 analyzes a part in which change in ΔFFR according to the predetermined regions RI1 to RI5 is large (an FFR value abruptly decreases) as a part in which constriction strongly affects blood flow. Accordingly, it is possible to more appropriately analyze the position of a blood vessel having high priority of treatment.

The analysis function 244 may perform fluid structure interaction (FSI) analysis for calculating a velocity distribution of blood flow in a blood vessel on the basis of the blood vessel shape model 256. The analysis function 244 may calculate an inner diameter constriction rate on the basis of inner diameters of blood vessels. In this case, the analysis function 244 may calculate an inner diameter constriction rate (% DS) using the lumen diameter of a blood vessel at each position of the blood vessel included in the blood vessel shape model 256.

The analysis function 244 may re-perform analysis when the generation function 243 has updated the blood vessel shape model 256 on the basis of a predetermined update condition. The update condition includes, for example a case where a contrast medium is injected by the aforementioned injector 118 or a case where setting of a medical member such as a stent inside a blood vessel according to an analysis result of image data captured by the first imaging system SA and the second imaging system SB is recognized.

Figure 10:
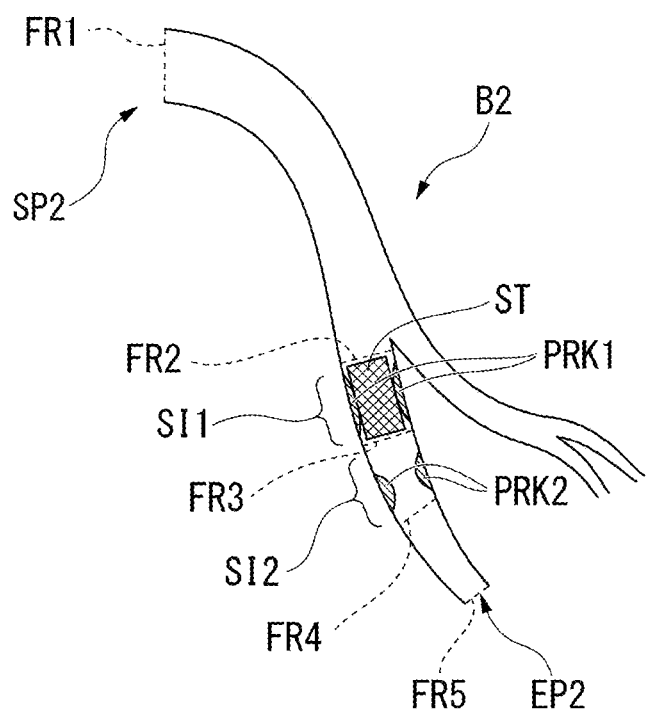
FIG. 10 is a diagram for describing a case where a stent is set in a blood vessel.

FIG. 10 is a diagram for describing a case where a stent is set in a blood vessel. The example of FIG. 10 shows a situation in which a stent ST is set in the constriction section SI1. In this case, since the moment at which the stent ST is set is a noncontrast state, the position of the blood vessel B2 cannot be confirmed from the image data 252 and only the stent ST is extracted. However, an imaging angle and the like when an image from which the stent ST is extracted is captured can be acquired from image data, and thus the analysis function 244 can identify the position of the stent in the blood vessel shape model 256 by collating the blood vessel shape model 256 generated from images captured at a plurality of imaging angles with the position of the stent ST at the current imaging angle. Accordingly, the generation function 243 updates some of image data on the basis of an imaging position immediately after the stent ST is set and regenerates the blood vessel shape model 256. That is, the generation function 243 acquires blood vessel related information at the position of the blood vessel in which the stent ST is set, updates the blood vessel shape model 256 on the basis of the acquired blood vessel related information, and stores the blood vessel shape model 256 in the memory irrespective of contrast and noncontrast. The generation function 243 may regenerate the blood vessel shape model 256 on the basis of pressure loss due to setting of a stent and other medical members.

The analysis function 244 can perform analysis of blood vessels with higher accuracy using the latest model information by performing analysis using the updated blood vessel shape model 256. The analysis function 244 may diagnose a symptom of the examination subject P, such as ischemic heart disease such as angina and cardiac infarction, according to the position and a degree of a lesion in a blood vessel on the basis of the above-described analysis result.

Furthermore, the analysis function 244 may derive fluid analysis results with respect to variations in cross-sectional areas or other pieces of blood vessel related information using machine learning, for example. Although a machine learning model in this case is a deep neural network (DNN) using a convolution neural network (CNN), the present invention is not limited thereto and any model may be used. When analysis results (for example, an FFR, ΔFFR, diagnostic results, and the like) are acquired using machine learning, the generation function 243 stores and learns a plurality of pieces of blood vessel related information about blood vessels in a model shape and information on analysis results with respect to the blood vessel related information, for example. More specifically, the analysis function 244 forms a discriminator which derives blood vessel related information and analysis results from a blood vessel shape model generated from images under operation by associating a blood vessel shape model generated from a blood vessel in a model shape with blood vessel related information and analysis results of the blood vessel, storing and learning the associated information, for example. It is possible to derive analysis results from a blood vessel shape model generated from image data according to machine learning by performing the aforementioned storage and learning on various blood vessel shapes.

The analysis function 244 causes the memory 250 to store the above-described analysis results as the analysis data 258.

Next, the display control function 245 will be described in detail. The display control function 245 causes the display 230 to display information about the above-described blood vessel shape model 256 and the analysis data 258. The display control function 245 may transmit the information about the blood vessel shape model 256 and the analysis data 258 to the medical image generation apparatus 100 via the communication interface 210 and cause the display 144 of the medical image generation apparatus 100 to display the information.

Figure 11:
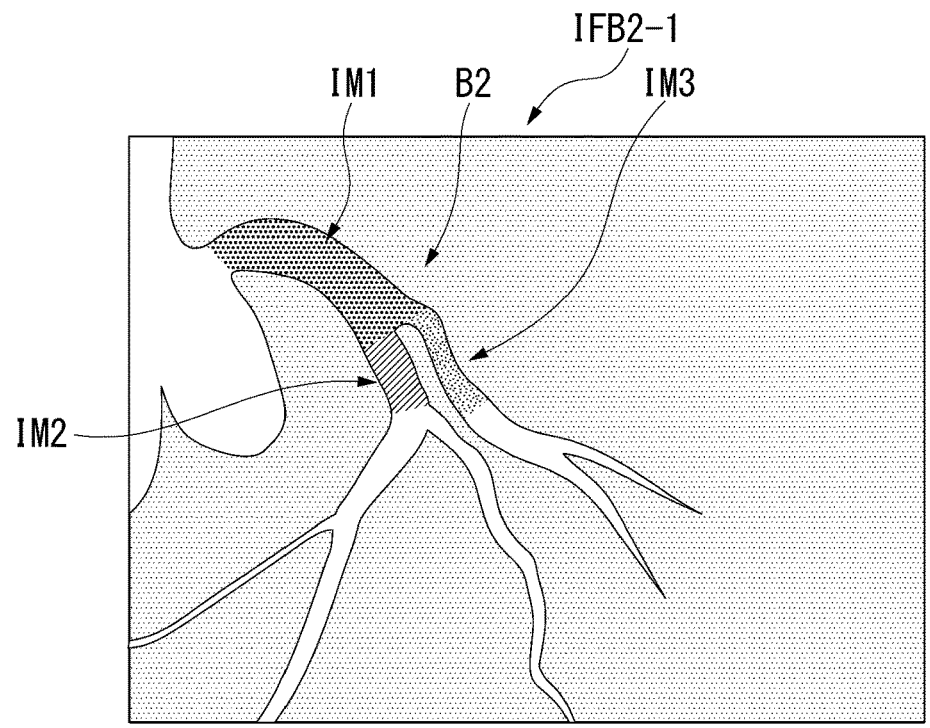
FIG. 11 is a diagram showing an example of an image displaying analysis results overlaid on an image captured in the medical image generation apparatus 100.

The display control function 245 may cause the display to display information about analysis results overlaid on one or both of images captured by the first imaging system SA and the second imaging system SB. FIG. 11 is a diagram showing an example of an image displaying analysis results overlaid on an image captured in the medical image generation apparatus 100. The example of FIG. 11 shows an image IFB2-1 in which images IM1 to IM3 based on analysis results are overlaid on a blood vessel image group image IFB2 with respect to the blood vessel B2 captured by the second imaging system SB. The display control function 245 performs coordinate transformation according to affine transformation or the like on the basis of three-dimensional position coordinates and an imaging range of the second imaging system SB when the blood vessel image group image IFB2 is captured, two-dimensional coordinates of the blood vessel B2 derived from an imaging angle and the like, and three-dimensional coordinates of the analysis data 258 to depict the analysis results in association with the two-dimensional coordinates of the blood vessel B2. In the example of FIG. 11, the images IM1 to 1M3 represented in shapes, colors, and the like associated with the analysis results and acquired FFR values are displayed in association with the positions thereof.

Figure 12:
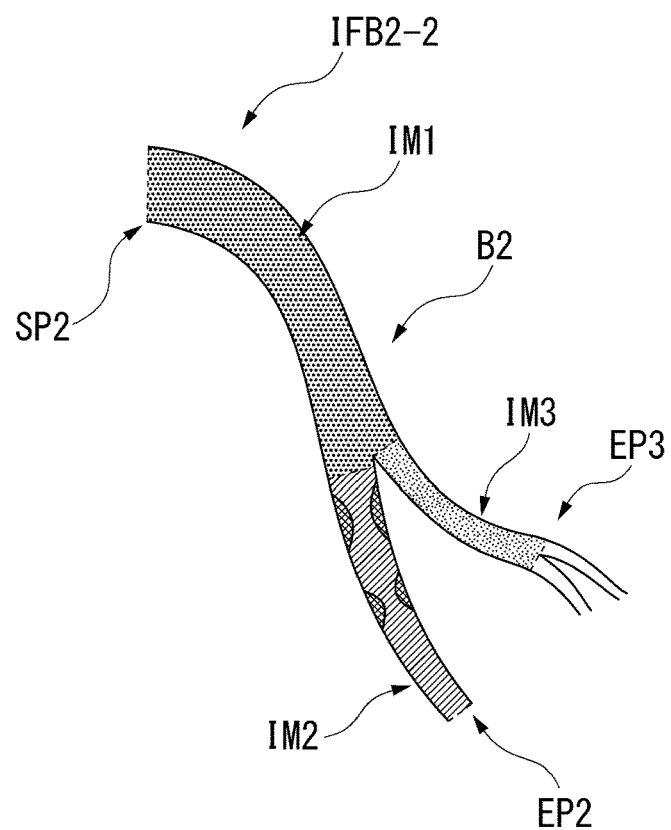
FIG. 12 is a diagram showing an example of an image IFB2-2 having an image of analysis results overlaid on reconstructed image data 254.

The display control function 245 may cause the display 230 or the display 144 to display an image of analysis results overlaid on the reconstructed image data 254 and the blood vessel shape model 256 generated by the medical image processing apparatus 200 instead of (or in addition to) the images captured by the first imaging system SA and the second imaging system SB. FIG. 12 is a diagram showing an example of an image IFB2-2 having an image of analysis results overlaid on the reconstructed image data 254. The example of FIG. 12 shows the image IFB2-2 in which the image of analysis results is overlaid on the image of the blood vessel B2. The display control function 245 associates three-dimensional coordinates of three-dimensional image data of the blood vessel B2 with three-dimensional coordinates of the analysis data 258 according to affine transformation or the like and causes the image based on the analysis result to be displayed at a corresponding position of the blood vessel B2 in an overlaid manner. In the example of FIG. 12, images IM1 to IM3 represented in shapes, colors, and the like associated with FFR values are displayed in association with the positions thereof as in FIG. 11. The display control function 245 may generate a corresponding image and display the image overlaid on a blood vessel image whenever the analysis data 258 is updated.

As shown in FIG. 11 and FIG. 12, the medical image processing apparatus 200 can allow a user or the like to easily intuitively ascertain a position conceived as a position at which constriction or plaque is present while viewing the image IFB2-1 and the image IFB2-2 or can support execution of appropriate treatment for the examination subject P by displaying an image associated with analysis results or diagnostic results overlaid on a blood vessel image. Although images associated with analysis results overlaid on blood vessel images are displayed in the examples of FIG. 11 and FIG. 12, a display mode is not limited thereto. For example, the display control function 245 may cause a display to display numerical values acquired as analysis results or text information of diagnostic results or cause an animation image representing blood flow corresponding to FFR values to be displayed in association with blood vessels.

[Processing Flow]

Figure 13:
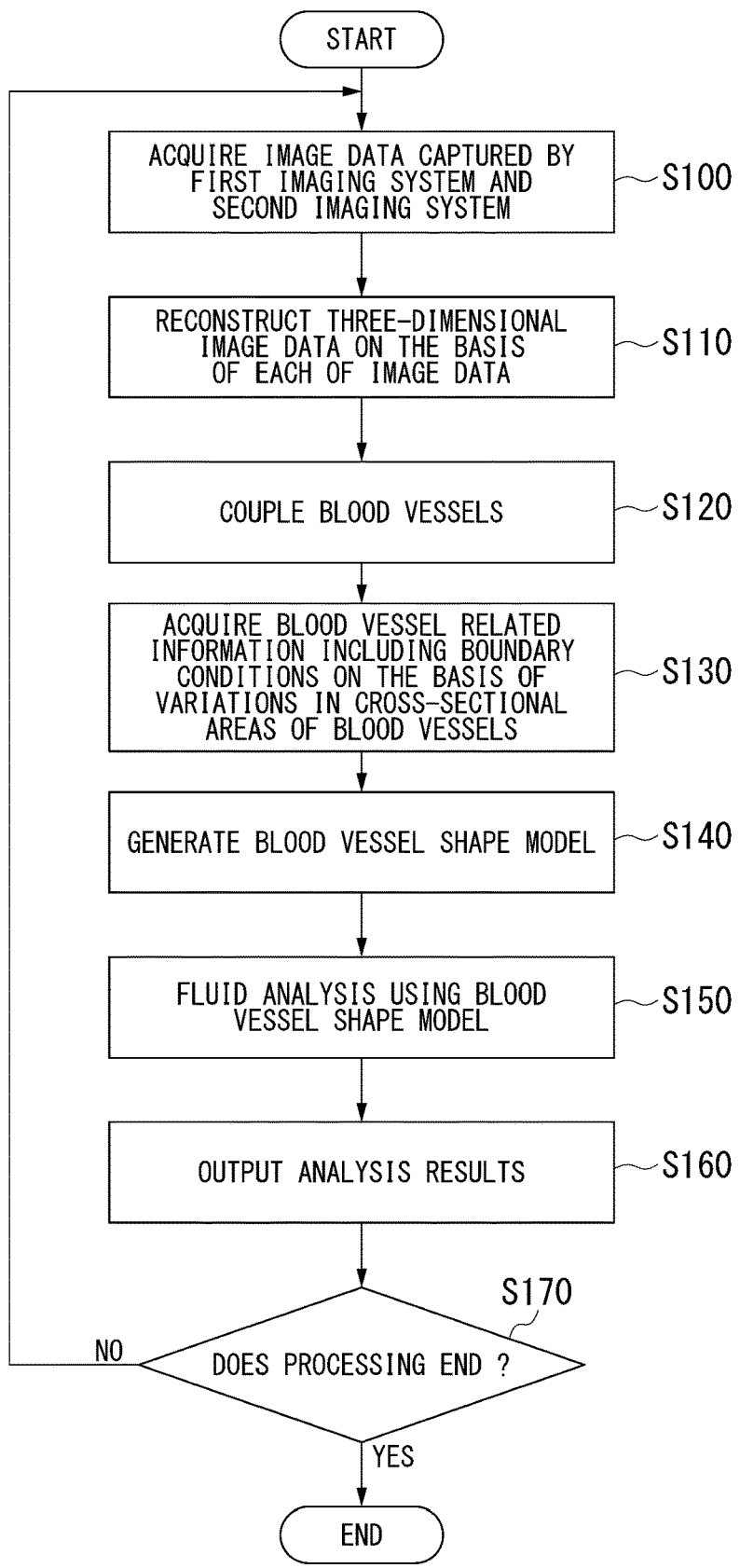
FIG. 13 is a flowchart showing a flow of a series of processes of processing circuitry 240 according to the first embodiment.

Hereinafter, a processing flow of the processing circuitry 240 in the first embodiment will be described. FIG. 13 is a flowchart showing a flow of a series of processes of the processing circuitry 240 according to the first embodiment. Execution of medical image processing using moving images (image group) captured by the first imaging system SA and the second imaging system SB will be described in the example below.

In the example of FIG. 13, the acquisition function 242 acquires image data captured by the first imaging system SA and the second imaging system SB (step S100).

Then, the generation function 243 reconstructs three-dimensional image data from the image data (step S110) and couples blood vessels when a distance between the fore-ends of the blood vessels included in the reconstructed three-dimensional image data (reconstructed image data) satisfies a predetermined condition (step S120). Subsequently, the generation function 243 acquires blood vessel related information including a boundary condition on the basis of the variations in cross-sectional areas of blood vessels on the basis of the reconstructed image data of the coupled blood vessels (step S130) and generates a blood vessel shape model including the acquired blood vessel related information and the reconstructed image data of the coupled blood vessels (step S140).

Next, the analysis function 244 performs fluid analysis using the blood vessel shape model 256 (step S150). Subsequently, the display control function 245 causes the display 144 or the display 230 to output analysis results acquired through fluid analysis and the like overlaid on a blood vessel image (step S160). Then, the processing circuitry 240 determines whether to end medical image processing (step S170). For example, in a case where image data cannot be acquired from the medical image generation apparatus 100 or an instruction for ending image processing is received through the input interface 220, the processing circuitry 240 determines that processing is ended and ends processing of this flowchart. In a case where the aforementioned condition is not satisfied and it is determined that processing is not ended in the process of step S170, processing returns to the process of step S100.

According to the above-described first embodiment, it is possible to perform blood vessel analysis in a shorter time by including the acquisition function 242 which acquires medical images including blood vessels of an examination subject, which have been captured in at least one direction at a plurality of points in time, the generation function 243 which generates a three-dimensional blood vessel shape model including variations in cross-sectional areas of blood vessels on the basis of the medical images acquired by the acquisition function 242, and the analysis function 244 which performs fluid analysis of blood flowing through the blood vessels on the basis of the blood vessel shape model generated by the generation function 243.

Second Embodiment

Hereinafter, a second embodiment will be described. The second embodiment is different from the first embodiment in that the boundary condition is analyzed on the basis of the variations in concentration of a contrast medium injected into blood vessels of an examination subject, instead of acquiring the boundary condition (for example, flow velocities and flow rates of blood flow in blood vessels) on the basis of the variations in cross-sectional areas of blood vessels according to the first embodiment. Accordingly, hereinafter, the above-described difference will be mainly described. Since components in a medical image processing system and a medical image processing apparatus according to the second embodiment may be the same as those of the medical image processing system 1 and the medical image processing apparatus 100 according to the first embodiment, the detail description will be omitted. This does the same with a third embodiment to be described later.

Figure 14:
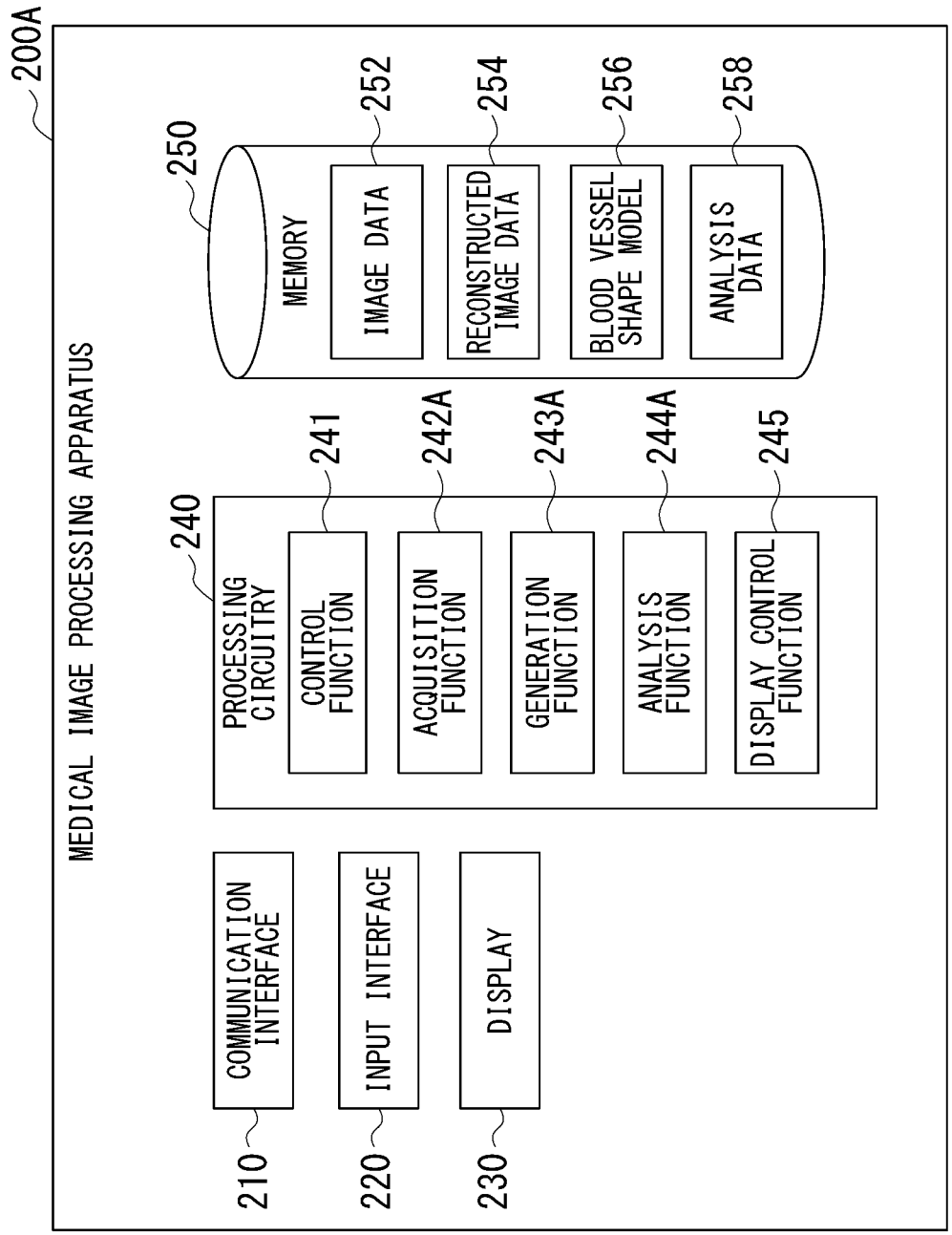
FIG. 14 is a diagram showing an example of a medical image generation apparatus 200A according to a second embodiment.

FIG. 14 is a diagram showing an example of a medical image generation apparatus 200A according to the second embodiment. The medical image generation apparatus 200A is different from the medical image generation apparatus 200 according to the first embodiment in that the medical image generation apparatus 200A includes an acquisition function 242A, a generation function 243A, and an analysis function 244A instead of the acquisition function 242, the generation function 243, and the analysis function 244.

The acquisition function 242A has a similar function to the acquisition function 242 in the first embodiment. Furthermore, the acquisition function 242A acquires information about a contrast medium injected into blood vessels of an examination subject. The information about the contrast medium includes, for example, information about an injection control of a contrast medium by the injector 118. The information about the injection control includes, for example, information about an amount, an injection speed, and an injection interval (intermittent time) of a contrast medium to be injected, and the like which are mechanically controlled. The information about the injection control is transmitted to the medical image generation apparatus 200A by, for example, the control function 151.

The generation function 243A has a similar function to the generation function 243 in the first embodiment. Furthermore, the generation function 243A acquires blood vessel related information at each position of a blood vessel on the basis of the reconstructed image data 254. The blood vessel related information according to the second embodiment may include information about a boundary condition at entrances and exits of flow paths analyzed by the analysis function 244A, predetermined other positions, and the like. The boundary condition includes flow velocities and flow rates of blood flow in blood vessels analyzed on the basis of the variations in concentration of a contrast medium in the blood vessels.

The generation function 243A generates the blood vessel shape model 256 in which the aforementioned blood vessel related information is associated with a three-dimensional blood vessel shape obtained by coupling blood vessels and causes the memory 250 to store the generated blood vessel shape model 256. The blood vessel shape model 256 is a three-dimensional blood vessel shape model including the boundary condition obtained from the variations in the concentration of the contrast medium in the blood vessels, and the like.

The analysis function 244A performs fluid analysis of blood flowing through a blood vessel using the blood vessel shape model 256. For example, the analysis function 244A acquires a flow rate and a flow velocity of the blood flowing through the blood vessel through fluid analysis at the position from variations in the concentration after injecting the contrast medium generated by the generation function 243A.

For example, the analysis function 244A analyzes the information about the variations in the concentration of the contrast medium at the predetermined position of the blood vessel by image analysis with respect to an X-ray image. Specifically, the analysis function 244A acquires the brightness value (reference brightness value) in the blood vessel from the image before the injection of the contrast medium, and then, analyzes the time-series variations in the brightness value after the injection of the contrast medium. For example, as the brightness value approaches the reference brightness value, as the concentration of the contrast medium decreases. In contrast, as the brightness value departs from the reference brightness value (specifically, the brightness value becomes lower than the reference brightness value), the concentration of the contrast medium increases. The analysis function 244A analyzes the information to obtain, as the concentration variations, the brightness variations from a time when the brightness value in the blood vessels varies after the injection of the contrast medium to a time when the brightness value becomes equal to the reference brightness value, or the brightness variations until a predetermined time elapses after the injection of the contrast medium. The analysis function 244A analyzes the flow velocities and flow rates of the contrast medium at a predetermined position on the basis of the analyzed concentration variations and the injection amount or the injection speed of the contrast medium from the injector 118 acquired by the acquisition function 242A. For example, the analysis function 244A may calculate the flow velocities and flow rates of the blood flow using a predetermined function in which the input values include concentration variations of a contrast medium and an injection amount and an injection speed of a contrast medium at a predetermined position, and the output values include flow velocities and flow rates of blood flow in blood vessel. The analysis function 244A may acquires the flow velocities and flow rates of the blood flow by referring a table in which flow velocities and flow rates of blood flow are associated with concentration variations, an injection amount, and an injection speed of a contrast medium.

The analysis function 244A may, instead of acquiring the injection amount from the control information of the injector 118 as described above, acquire the injection amount by multiplying the cross-sectional area of a blood vessel which is an inlet of a contrast medium by an injection speed, and acquire the flow rate of blood flow on the basis of the acquired injection amount.

[Processing Flow]

Figure 15:
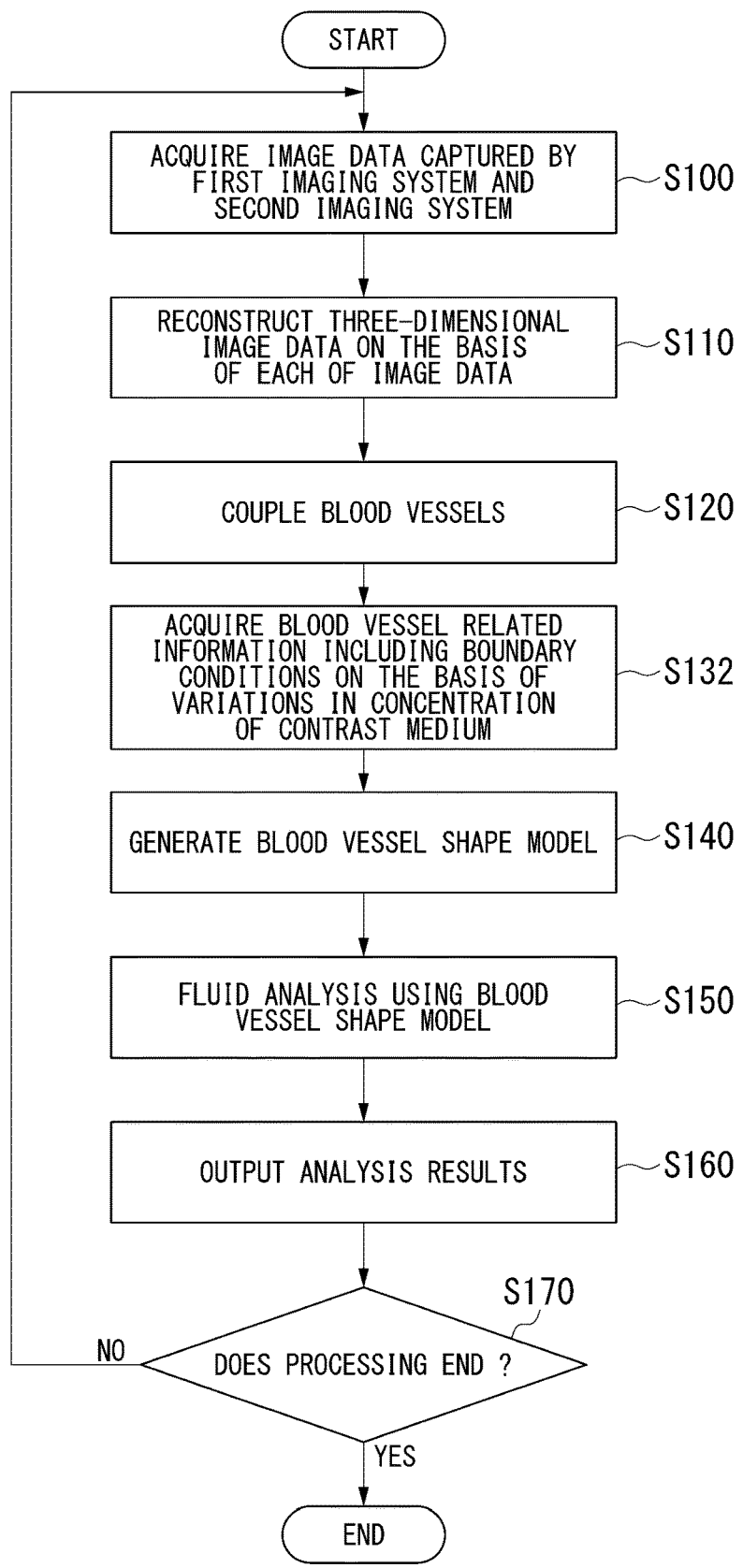
FIG. 15 is a flowchart showing a flow of a series of processes of processing circuitry 240 according to the second embodiment.

Hereinafter, a processing flow of the processing circuitry 240 in the second embodiment will be described. FIG. 15 is a flowchart showing a flow of a series of processes of processing circuitry 240 according to the second embodiment. The processing shown in FIG. 15 is different from the processing of the steps S100 to S170 shown in FIG. 13 in that the processing shown in FIG. 15 includes a step S132 instead of the step S130. Accordingly, hereinafter, the processing of the step S132 will be mainly described.

In an example in FIG. 15, the generation function 243A acquires the blood vessel related information including the boundary condition (flow rates of blood flow in blood vessels, and the like) obtained on the basis of the variations in the concentration of the contrast medium (step S132). Next, the generation function 243A generates the blood vessel shape model including the boundary condition obtained from the variations in the concentration of the contrast medium on the basis of the acquired blood vessel related information and the reconstructed image data of the coupled blood vessels (step S140. Then, the analysis function 244A performs fluid analysis using the blood vessel shape model 256 (step S150).

According to the above-described second embodiment, as with the first embodiment, it is possible to perform blood vessel analysis in a shorter time by acquiring the boundary condition from the variations in the concentration of the contrast medium in the blood vessels and performing the analysis using the blood vessel shape model including the acquired boundary condition.

Third Embodiment

Hereinafter, a third embodiment will be described. The third embodiment is different from the first and second embodiments in that a boundary condition on the basis of variations in cross-sectional areas of blood vessels and a boundary condition on the basis of variations in concentration of a contrast medium in blood vessels are acquired and fluid analysis of blood vessels is performed on the basis of each of the acquired boundary conditions. Hereinafter, the above-described difference will be mainly described.

Figure 16:
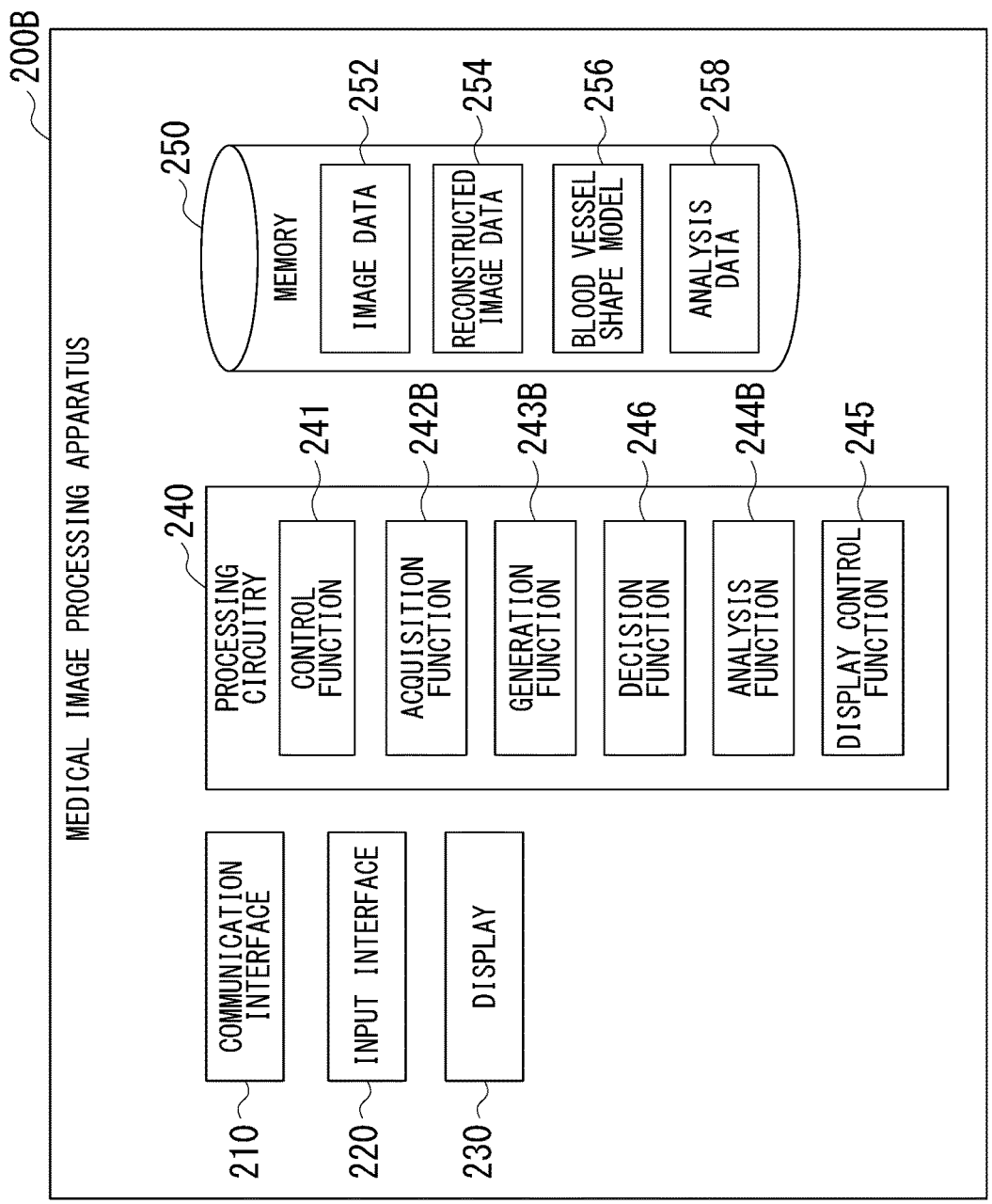
FIG. 16 is a diagram showing an example of a medical image generation apparatus 200B according to a third embodiment.

FIG. 16 is a diagram showing an example of a medical image generation apparatus 200B according to the third embodiment. The medical image generation apparatus 200B is different from the medical image generation apparatus 200 according to the first embodiment in that the medical image generation apparatus 200B includes an acquisition function 242B, a generation function 243B, a decision function 246, and an analysis function 244B instead of the acquisition function 242, the generation function 243, and the analysis function 244.

The acquisition function 242B has a similar function to the acquisition function 242A according to the second embodiment. The generation function 243B acquires a boundary condition (a first boundary condition) on the basis of variations in cross-sectional areas of blood vessels as the generation function 243 according to the first embodiment. Furthermore, the generation function 243B acquires a boundary condition (a second boundary condition) on the basis of variations in concentration of a contrast medium in blood vessels as the generation function 243A according to the second embodiment. Furthermore, the generation function 243B acquires blood vessel related information including a boundary condition obtained from any one or both of the first boundary condition and the second boundary condition as the decision result by the decision function 246. The generation function 243B generates a blood vessel shape model 256 including the blood vessel related information. The analysis function 244B performs fluid analysis using the blood vessel shape model 256 generated by the generation function 243B.

The decision function 246 decides a boundary condition to be included in the blood vessel related information on the basis of the first boundary condition or the second boundary condition. For example, the decision function 246 decides that the variations in cross-sectional areas are not accurately recognized in a case where the variations in cross-sectional areas of blood vessels are out of a predetermined range when acquiring the first boundary condition, and decides that the second boundary condition is to be included in the blood vessel related information. The decision function 246 decides that the variations in concentration are not accurately recognized in a case where the concentration of a contrast medium (the brightness of an X-ray image) is out of a predetermined concentration range (brightness range), and decides that the first boundary condition is to be included in the blood vessel related information. The decision function 246 may decide that the average of the first boundary condition and the second boundary condition is to be included in the blood vessel related information. The decision function 246 may decide one of the first boundary condition and the second boundary condition which has higher predetermined priority, as a boundary condition to be included in the blood vessel related information. In this case, for example, the decision function 246 compares the results obtained by performing fluid analysis using each of the boundary conditions, and decides priority to be used from next time on the basis of the comparison result. The aforementioned decision of the boundary condition may be performed for each analysis range of blood vessels, or may be performed for a plurality of analysis ranges at once.

[Processing Flow]

Figure 17:
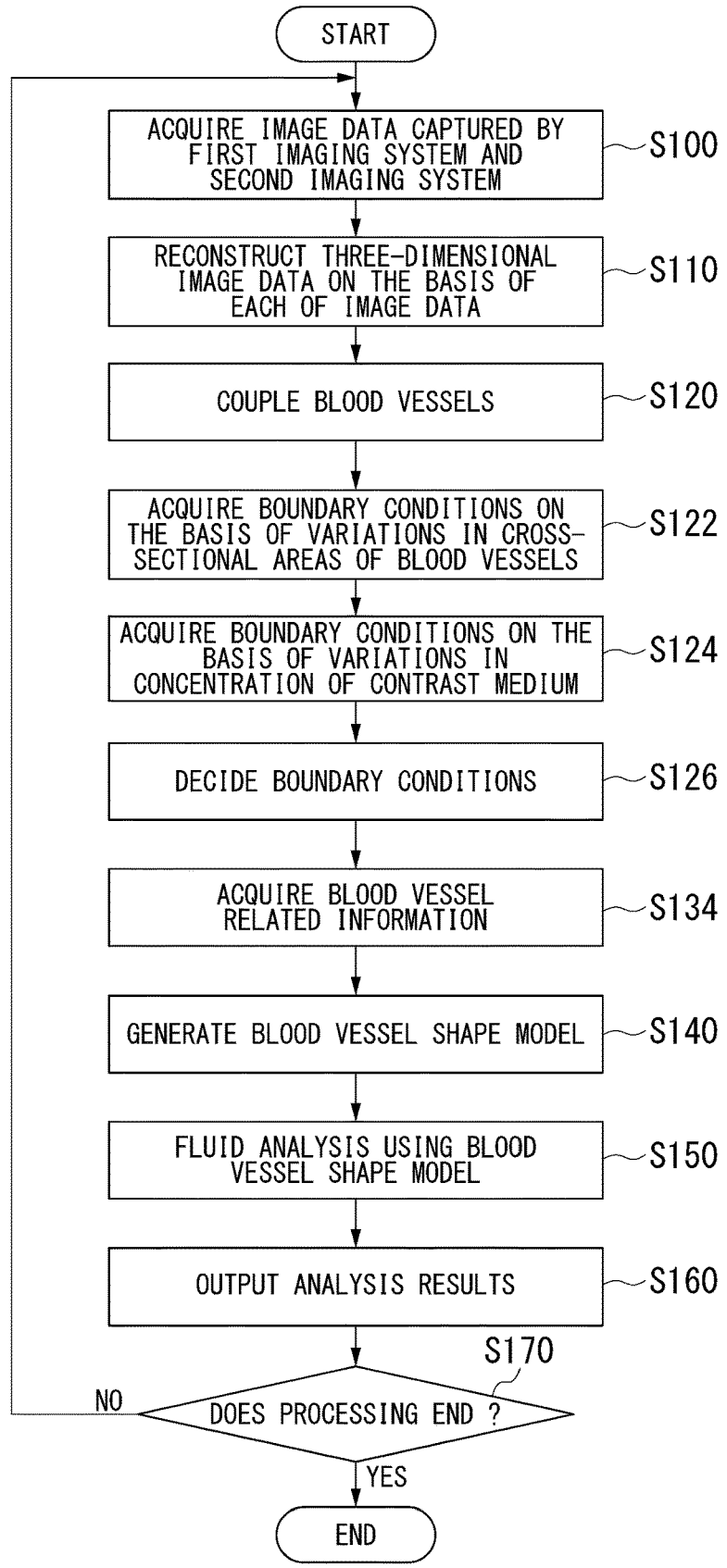
FIG. 17 is a flowchart showing a flow of a series of processes of processing circuitry 240 according to the third embodiment.

Hereinafter, a processing flow of the processing circuitry 240 in the third embodiment will be described. FIG. 17 is a flowchart showing a flow of a series of processes of processing circuitry 240 according to the third embodiment. The processing shown in FIG. 17 is different from the processing in the steps S100 to S170 shown in FIG. 13 in that the processing shown in FIG. 17 includes steps S122 to S126 and S134 instead of the step S130. Accordingly, hereinafter, the processing of the steps S122 to S126 and S134 will be mainly described.

In an example in FIG. 17, after the processing of the step S120, the generation function 243B acquires the first boundary condition on the basis of variations in cross-sectional areas of blood vessels and the second boundary condition on the basis of variations in concentration of a contrast medium (steps S122, S124). Next, the decision function 246 decides a boundary condition to be included in the blood vessel related information on the basis of the first boundary condition and the second boundary condition (S126). Next, the generation function 243B generates the blood vessel related information including the decided boundary condition (step S134), and generates a blood vessel shape model on the basis of the generated blood vessel related information and the reconstructed image data of the coupled blood vessels (step S140).

According to the above-described third embodiment, in addition to similar effects to the first and second embodiments, it is possible to decide a more appropriate boundary condition and to generate the blood vessel shape model including the blood vessel related information on the basis of the first boundary condition and the second boundary condition. Furthermore, according to the above-described third embodiment, it is possible to perform a more appropriate fluid analysis for each branch by, for example, deciding the first boundary condition and the second boundary condition for each analysis range of blood vessels (for example, for each branch). Accordingly, it is possible to realize high-accuracy fluid analysis.

According to the above-described embodiments, it is possible to reduce time, effort and burden required to capture other images for generating a model for analysis by generating a blood vessel shape model using blood vessel images (images captured by injecting a contrast medium into a blood vessel) captured in order to observe shapes of blood vessels of an examination subject under operation and performing blood vessel analysis using the generated model, and thus it is possible to generate a blood vessel shape model in real time and perform analysis. More specifically, although there are conventional methods such as FFR analysis using computed tomography (CT) images, quantitative flow ratio (QFR) analysis, and wire-FFR in which a pressure wire is inserted into a coronary artery during instillation of a coronary extension agent (adenosine) to measure an FFR, for example, CT-FFR is not suitable in an acute phase because it requires preoperative CT imaging, QFR requires time and effort for measurement of thrombolysis in myocardial infarction (TIMI) frame count, and Wire-FFR requires time and effort for the procedure itself. Accordingly, any method is not effective for ischemia determination in an acute stage. In each embodiment, it is possible to perform analysis and diagnosis such as ischemia determination more rapidly by generating a blood vessel shape model for performing analysis of FFR and the like from angiography (angiographic images) generally captured under operation, for example, and deriving an FFR and the like from the generated blood vessel shape model.

Although it is desirable to use blood vessel images captured in two or more directions in order to construct a more accurate three-dimensional model in generation of a blood vessel shape model in the above-described embodiments, the present invention is not limited thereto and a blood vessel shape model may be generated using only blood vessel images captured in one direction and analysis using the generated model may be performed. Further, when imaging is performed in one direction, a certain degree of analysis accuracy can be secured even when only imaging in one direction is performed by determining an imaging direction such that the blood vessel of an imaging target is mostly perpendicular to the imaging direction. In addition, when only images captured in one direction are used, the configuration of one of the first imaging system SA and the second imaging system SB in the above-described medical image generation apparatus 100 may not be provided. Moreover, when images captured in three or more directions are used, the medical image generation apparatus 100 may include three or more imaging systems corresponding to the number of directions.

Any one of the above-described embodiments can be represented as follows.

A medical image processing apparatus including:
a storage configured to store a program; and
a processor,
wherein the processor is configured, by executing the program:
to acquire time-series medical images including blood vessels of an examination subject, the time-series medical images being fluoroscopically captured in at least one direction at a plurality of points in time;
to generate a blood vessel shape model including time-series variation information about the blood vessels in an analysis region of the blood vessels on the basis of the acquired time-series medical images; and
to perform fluid analysis of blood flowing through the blood vessels on the basis of the generated blood vessel shape model.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured to:
   acquire a plurality of time-series medical images including a plurality of blood vessels of an examination subject, the plurality of time-series medical images being fluoroscopically captured in at least one direction at a plurality of points in time;
   generate, based on the plurality of time-series medical images, a blood vessel shape model including time-series variation information about the plurality of blood vessels in an analysis region;
   perform, based on the blood vessel shape model, a fluid analysis of blood flowing through the blood vessels,
   synchronize the plurality of time-series medical images based on electrocardiogram data of the examination subject to reconstruct a three-dimensional medical image with respect to the plurality of blood vessels;
   estimate a first position of a first end of a first blood vessel and a second position of a second end of a second blood vessel different from the first blood vessel, the first blood vessel and the second blood vessel being included in the analysis region of the three-dimensional medical image; and
   generate the blood vessel shape model by coupling the first end and the second end in a case where the first position and the second position are entrances of blood flow paths, and a distance on three-dimensional coordinates between the first end and the second end is equal to or less than a predetermined distance.

2. The medical image processing apparatus according to claim 1, wherein the processing circuitry is further configured to:
acquire, as the time-series variation information, a first variation in cross-sectional area of each of the plurality of blood vessels;
decide a first boundary condition of the fluid analysis based on the first variation; and
perform the fluid analysis based on the blood vessel shape model including the first boundary condition.

3. The medical image processing apparatus according to claim 1, wherein the processing circuitry is further configured to:
acquire, as the time-series variation information, a second variation in concentration of a contrast medium injected into the plurality of blood vessels in the analysis region;
decide a second boundary condition of the fluid analysis based on the second variation; and
perform the fluid analysis based on the blood vessel shape model including the second boundary condition.

4. The medical image processing apparatus according to claim 1, wherein the processing circuitry is further configured to:
acquire, as the time-series variation information, a first variation in cross-sectional area of each of the plurality of blood vessels and a second variation in concentration of a contrast medium injected into the plurality of blood vessels in the analysis region;
decide a first boundary condition and a second boundary condition of the fluid analysis based respectively on the first variation and the second variation; and
generate the blood vessel shape model based on the first boundary condition and the second boundary condition.

5. The medical image processing apparatus according to claim 1, wherein the processing circuitry is further configured to:
estimate the entrances of the blood flow paths based on a change in position of a contrast medium injected into the plurality of blood vessels included in the plurality of time-series medical images.

6. The medical image processing apparatus according to claim 1, wherein the processing circuitry is further configured to:
determine that the first end and the second end have been coupled to each other in a case where a third blood vessel or a medical member is present between the first end and the second end, the third blood vessel being different from the first blood vessel and the second blood vessel.

7. The medical image processing apparatus according to claim 1, wherein the processing circuitry is further configured to:
correct at least one of a first size of the first blood vessel and a second size of the second blood vessel, based on a third blood vessel different from the first blood vessel and the second blood vessel, or a human body structure around the first blood vessel and the second blood vessel.

8. The medical image processing apparatus according to claim 1, wherein the processing circuitry is further configured to:
estimate, based on diameters of the first blood vessel and the second blood vessel included in the three-dimensional medical image, a third position of a third end of the first blood vessel and a fourth position of a fourth end of the second blood vessel; and
generate the blood vessel shape model including a first blood flow path and a second blood flow path, the first blood flow path extending from the first end to the third end, and the second blood flow path extending from the second end to the fourth end.

9. The medical image processing apparatus according to claim 1, wherein the processing circuitry is further configured to:
update the blood vessel shape model in a case where it is estimated that a medical member has been set in at least one of the plurality of blood vessels included in the plurality of time-series medical images.

10. The medical image processing apparatus according to claim 1, wherein the processing circuitry is further configured to:
display an image with respect to a result of the fluid analysis using the blood vessel shape model, the image being overlaid on the plurality of blood vessels included in the plurality of time-series medical images.

11. A non-transitory computer-readable storage medium storing a program, the program causing a computer of a medical image processing apparatus to:
acquire a plurality of time-series medical images including a plurality of blood vessels of an examination subject, the plurality of time-series medical images being fluoroscopically captured in at least one direction at a plurality of points in time;
generate, based on the plurality of time-series medical images, a blood vessel shape model including time-series variation information about the plurality of blood vessels in an analysis region;
perform, based on the blood vessel shape model, a fluid analysis of blood flowing through the blood vessels,
synchronize the plurality of time-series medical images based on electrocardiogram data of the examination subject to reconstruct a three-dimensional medical image with respect to the plurality of blood vessels;
estimate a first position of a first end of a first blood vessel and a second position of a second end of a second blood vessel different from the first blood vessel, the first blood vessel and the second blood vessel being included in the analysis region of the three-dimensional medical image; and
generate the blood vessel shape model by coupling the first end and the second end in a case where the first position and the second position are entrances of blood flow paths, and a distance on three-dimensional coordinates between the first end and the second end is equal to or less than a predetermined distance.

12. A medical image processing method comprising:
acquiring a plurality of time-series medical images including a plurality of blood vessels of an examination subject, the plurality of time-series medical images being fluoroscopically captured in at least one direction at a plurality of points in time;
generating, based on the plurality of time-series medical images, a blood vessel shape model including time-series variation information about the plurality of blood vessels in an analysis region; and
performing, based on the blood vessel shape model, a fluid analysis of blood flowing through the plurality of blood vessels;
synchronizing the plurality of time-series medical images based on electrocardiogram data of the examination subject to reconstruct a three-dimensional medical image with respect to the plurality of blood vessels;

estimating a first position of a first end of a first blood vessel and a second position of a second end of a second blood vessel different from the first blood vessel, the first blood vessel and the second blood vessel being included in the analysis region of the three-dimensional medical image; and generating the blood vessel shape model by coupling the first end and the second end in a case where the first position and the second position are entrances of blood flow paths, and a distance on three-dimensional coordinates between the first end and the second end is equal to or less than a predetermined distance.

13. The medical image processing method according to claim 12, further comprising:

acquiring, as the time-series variation information, at least one of a first variation in a cross-sectional area of each of the plurality of blood vessels and a second variation in concentration of a contrast medium injected into the plurality of blood vessels in the analysis region;

deciding at least one of a first boundary condition and a second boundary condition of the fluid analysis based respectively on the first variation and the second variation; and performing the fluid analysis based on the blood vessel shape model including the at least one of the first boundary condition and the second boundary condition.

14. The medical image processing method according to claim 12, further comprising:

estimating the entrances of the blood flow paths based on a change in position of a contrast medium injected into the plurality of blood vessels.

15. The medical image processing method according to claim 12, further comprising:

determining that the first end and the second end have been coupled to each other in a case where a third blood vessel or a medical member is present between the first end and the second end, the third blood vessel being different from the first blood vessel and the second blood vessel.

16. The medical image processing method according to claim 12, further comprising:

correcting at least one of a first size of the first blood vessel and a second size of the second blood vessel, based on a third blood vessel different from the first blood vessel and the second blood vessel, or a human body structure around the first blood vessel and the second blood vessel.

17. The medical image processing method according to claim 12, further comprising:

estimating, based on diameters of the first blood vessel and the second blood vessel included in the three-dimensional medical image, a third position of a third end of the first blood vessel and a fourth position of a fourth end of the second blood vessel; and generating the blood vessel shape model including a first blood flow path and a second blood flow path, the first blood flow path extending from the first end to the third end, and the second blood flow path extending from the second end to the fourth end.

18. The medical image processing method according to claim 12, further comprising:

updating the blood vessel shape model in a case where it is estimated that a medical member has been set in at least one of the plurality of blood vessels.

* * * * *

UNITED STATES PATENT AND TRADEMARK OFFICE
CERTIFICATE OF CORRECTION

PATENT NO. : 11,481,957 B2
APPLICATION NO. : 16/833732
DATED : October 25, 2022
INVENTOR(S) : Hideaki Ishii It is certified that error appears in the above-identified patent and that said Letters Patent is hereby corrected as shown below:

On the Title Page

Item (54) and in the Specification, Column 1, Lines 1-2, the Title should read as follows:
--MEDICAL IMAGE PROCESSING APPARATUS, MEDICAL IMAGE PROCESSING METHOD, AND STORAGE MEDIUM--

Signed and Sealed this
Thirty-first Day of January, 2023

Katherine Kelly Vidal
Director of the United States Patent and Trademark Office